(12) United States Patent
Pouzet et al.

(10) Patent No.: US 9,150,586 B2
(45) Date of Patent: Oct. 6, 2015

(54) PIPERIDINO-DIHYDROTHIENOPYRIMIDINE SULFOXIDES AND THEIR USE FOR TREATING COPD AND ASTHMA

(75) Inventors: Pascale A. J. Pouzet, Biberach an der Riss (DE); Peter Nickolaus, Warthausen (DE); Ulrike Werthmann, Biberach an der Riss (DE); Rogelio P. Frutos, Sandy Hook, CT (US); Bing-Shiou Yang, Southbury, CT (US); Soojin Kim, Demarest, NJ (US); Jason Alan Mulder, New Milford, CT (US); Nitinchandra Patel, Danbury, CT (US); Chris H. Senanayake, Brookfield, CT (US); Thomas G. Tampone, Southbury, CT (US); Xudong Wei, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/239,818

(22) PCT Filed: Mar. 15, 2012

(86) PCT No.: PCT/EP2012/066104
§ 371 (c)(1),
(2), (4) Date: May 1, 2014

(87) PCT Pub. No.: WO2013/026797
PCT Pub. Date: Feb. 28, 2013

(65) Prior Publication Data
US 2015/0148322 A1    May 28, 2015

Related U.S. Application Data

(60) Provisional application No. 61/526,861, filed on Aug. 24, 2011.

(51) Int. Cl.
C07D 239/02    (2006.01)
C07D 495/04    (2006.01)
C07D 401/04    (2006.01)
C07C 213/00    (2006.01)
A61K 31/519   (2006.01)
A61K 45/06    (2006.01)

(52) U.S. Cl.
CPC ............ *C07D 495/04* (2013.01); *A61K 31/519* (2013.01); *A61K 45/06* (2013.01); *C07C 213/00* (2013.01); *C07D 401/04* (2013.01); *C07B 2200/13* (2013.01)

(58) Field of Classification Search
None
See application file for complete search history.

(56) References Cited

U.S. PATENT DOCUMENTS

| 3,318,881 A | 5/1967 | Ohnacker et al. |
| 3,318,883 A | 5/1967 | Ohnacker et al. |
| 3,763,156 A | 10/1973 | Horch et al. |
| 3,838,121 A | 9/1974 | Woitun et al. |
| 4,256,737 A | 3/1981 | Nestor et al. |
| 4,256,738 A | 3/1981 | Woitun et al. |
| 5,187,168 A | 2/1993 | Primeau et al. |
| 7,019,013 B2 | 3/2006 | Eggenweiler et al. |
| 7,511,045 B2 | 3/2009 | Hoenke et al. |
| 7,723,341 B2 | 5/2010 | Hoenke et al. |
| 7,960,422 B2 | 6/2011 | Arzel et al. |
| 8,114,878 B2 | 2/2012 | Pouzet et al. |

(Continued)

FOREIGN PATENT DOCUMENTS

| AR | 053235 | 4/2006 |
| AU | 2006237354 A1 | 10/2006 |

(Continued)

OTHER PUBLICATIONS

International Search Report for PCT/EP2012/066104, date of mailing Jan. 30, 2013.

(Continued)

*Primary Examiner* — Jeffrey H Murray
(74) *Attorney, Agent, or Firm* — Michael P. Morris; Timothy X. Witkowski

(57) ABSTRACT

The invention relates to novel piperidino-dihydrothienopyrimidine sulfoxides of formula I,

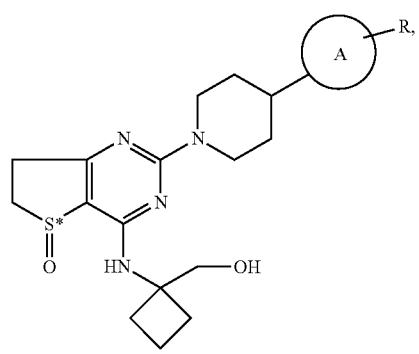

wherein Ring A is a 6-membered aromatic ring which may optionally comprise one or two nitrogen atoms and
wherein R is Cl and
wherein R may be located either in the para-, meta- or ortho-position of Ring A,
wherein S* is a sulphur atom that represents a chiral center, and all pharmaceutically acceptable salts, enantiomers and racemates, hydrates and solvates thereof and the use of these compounds for the treatment of inflammatory or allergic diseases of the respiratory tract such as COPD or asthma.

3 Claims, 10 Drawing Sheets

(56) References Cited

U.S. PATENT DOCUMENTS

Figure 1A:
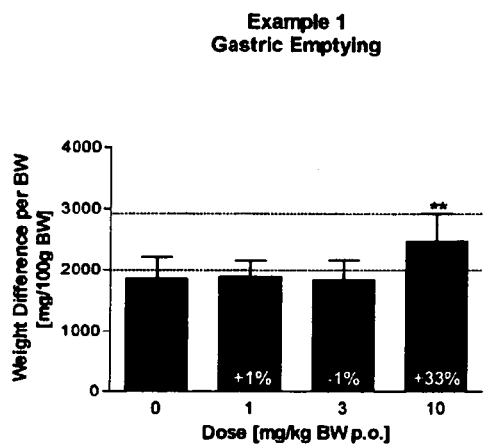

| | | | |
|---|---|---|---|
| 8,354,531 | B2 | 1/2013 | Hoenke et al. |
| 8,609,670 | B2 | 12/2013 | Pouzet et al. |
| 2003/0016795 | A1 | 1/2003 | Brandenberger |
| 2007/0259846 | A1 | 11/2007 | Hoenke et al. |
| 2008/0032358 | A1 | 2/2008 | Behrens et al. |
| 2008/0096882 | A1 | 4/2008 | Pouzet et al. |
| 2009/0131454 | A1 | 5/2009 | Arzel et al. |
| 2010/0137282 | A1 | 6/2010 | Davies et al. |
| 2010/0197656 | A1 | 8/2010 | Hoenke et al. |
| 2010/0222585 | A1 | 9/2010 | Frutos et al. |
| 2010/0273793 | A1 | 10/2010 | Nemecek et al. |
| 2010/0305102 | A1 | 12/2010 | Pouzet et al. |
| 2011/0021501 | A1 | 1/2011 | Pouzet et al. |
| 2011/0028441 | A1 | 2/2011 | Pouzet et al. |
| 2011/0046096 | A1 | 2/2011 | Pouzet et al. |
| 2011/0123435 | A1 | 5/2011 | Siddiqui et al. |
| 2012/0028932 | A1 | 2/2012 | Nickolaus et al. |
| 2012/0035143 | A1 | 2/2012 | Nickolaus et al. |
| 2012/0108534 | A1 | 5/2012 | Pouzet et al. |

FOREIGN PATENT DOCUMENTS

| | | | |
|---|---|---|---|
| CA | 2605161 | A1 | 10/2006 |
| CA | 2647243 | A1 | 10/2007 |
| CA | 2705414 | A1 | 4/2009 |
| DE | 1940572 | A1 | 2/1971 |
| DE | 2112950 | A1 | 10/1971 |
| DE | 2032687 | A1 | 1/1972 |
| DE | 2121950 | A1 | 11/1972 |
| DE | 102005019201 | A1 | 11/2006 |
| EP | 0806418 | A2 | 11/1997 |
| EP | 0899263 | A2 | 3/1999 |
| EP | 1847543 | A1 | 10/2007 |
| FR | 1603313 | A | 4/1971 |
| GB | 1072414 | A | 6/1967 |
| JP | 07330777 | A | 12/1995 |
| JP | 2004516329 | A | 6/2004 |
| JP | 200503345 | | 2/2005 |
| WO | 02088138 | A1 | 11/2002 |
| WO | 03055890 | | 7/2003 |
| WO | 03059913 | | 7/2003 |
| WO | 2004096810 | A1 | 11/2004 |
| WO | 2005094033 | A1 | 6/2005 |
| WO | 2005082865 | A1 | 9/2005 |
| WO | 2006111549 | A1 | 10/2006 |
| WO | 2007118793 | A1 | 10/2007 |
| WO | 2008128942 | A1 | 10/2008 |
| WO | 2009050236 | A1 | 4/2009 |
| WO | 2009050242 | A2 | 4/2009 |
| WO | 2009050248 | A1 | 4/2009 |
| WO | 2009051556 | A1 | 4/2009 |
| WO | 2009052138 | A1 | 4/2009 |
| WO | 2009052288 | A1 | 4/2009 |
| WO | 2009053268 | A1 | 4/2009 |
| WO | 2009087305 | A1 | 7/2009 |
| WO | 2010097332 | A1 | 9/2010 |
| WO | 2010097334 | A1 | 9/2010 |

OTHER PUBLICATIONS

Brown, W.M., "Treating COPD with PDE 4 Inhibitors", International Journal of COPD, 2007, vol. 2 (4), pp. 517-533.

Chakraborti et al.; 3D-QSAR Studies on Thieno[3,2-d]pyrimidines as Phosphodiesterase IV Inhibitors; Bioorganic & Medicinal Chemistry Letters; 2003; vol. 13; pp. 1403-1408.

Crespo, Maria, I., et al; Design, Synthesis, and Biological Activities of New Thieno[3,2-d]pyrimidines as Selective Type 4 Phosphodiesterase Inhibitors; J. Medicinal Chemistry (1998) vol. 41 pp. 4021-4035.

DiGirolamo, G, et al; Effects of Cyclooxygenase Inhitor Pretreatment on Nitric Oxide production, nNOS and iNOS Expression in Rat Cerebellum; British Journal of Pharmacology (2003) vol. 139, No. 6 pp. 1164-1170.

Inernational Search Report, Form PCT/ISR/210, for corresponding application PCT/EP2008/063747 date of mailing Mar. 4, 2009.

International Search Report for PCT/EP2008/063970 mailed Apr. 1, 2009.

International Search Report Form PCT/ISA/210, for corresponding application PCT/EP2007/053255 date of mailing Jul. 9, 2007.

International Search Report, for PCT/EP2008/063999; date of mailing: Apr. 1, 2009.

International Search Report, Form PCT/ISA/210, and written opinion, form PCT/ISA/237, corresponding application PCT/EP2008/063983 mailing date Jun. 2, 2009.

Kolosionek, E. et al., "Expression and Activity of Phosphodiesterase Isoforms during Epithelial Mesenchymal Transition: The Role of Phosphodiesterase 4", Molecular Biology of the Cell, 2009, vol. 20, pp. 4751-4765.

Kumar, N., et al., "Phosphodiesterase 4-Targeted treatments for autoimmune diseases", BMC Medicine, 2013. vol. 20, pp. 4751-4765.

Odingo, Joshua; Inhibitors of PDE4: A Review of Recent Patent Literature; Expert Opinion (2005) vol. 15; No. 7 pp. 773-787.

Salari-Sharif, P., et al., "Phosphodiesterase 4 Inhibitors in Inflammatory Bowel Disease: A Comprehensive Review", Current Pharmaceutical Design, 2010, vol. 16, pp. 3661-3667.

Vippagunta, et al., "Crystalline Solids", Advanced Drug Delivery Reviews, V. 48, 2001, p. 3-26.

Gavezzoti, A., "Are Crystal Structures Predicatable?" Accounts of Chemical Research. v. 27, 1994, p. 309-314.

International Search Report PCT/EP2007/053255, mailed Jun. 29, 2007.

Banner, et al., Trenda in Pharmacalogical Sciences, vol. 25, No. 8, "PDE4 inhibition: a novel approach for the treatment of inflammatory bowel disease", 2004.

Murata et al., Clinical and Experimental Metastasis, "Cyclic AMP specific phosphodieterase activity and colon cancer cell motility", vol. 18, p. 599-604, 2001.

Vignola, Respiratory Medicine, "PDE4 inhibitors in COPD-a more selective approach to treatment", vol. 98, p. 495-503, 2004.

Huang, et al., Current Opinion in Chemical Biology, "The next generation of PDE4 inhibitors", vol. 5, p. 432-438, 2001.

Spina, Current Opinion in Investigational Drugs, "The potential of PDE4 inhibitors in asthma or COPD", vol. 1, p. 204-213. 2000.

Udalov, et al., BMC Pulmonary Medicine, "Effects of phosphodieterase 4 inhibition on bleomycin-induced pulmonary fibrosis in mice", vol. 10, 2010.

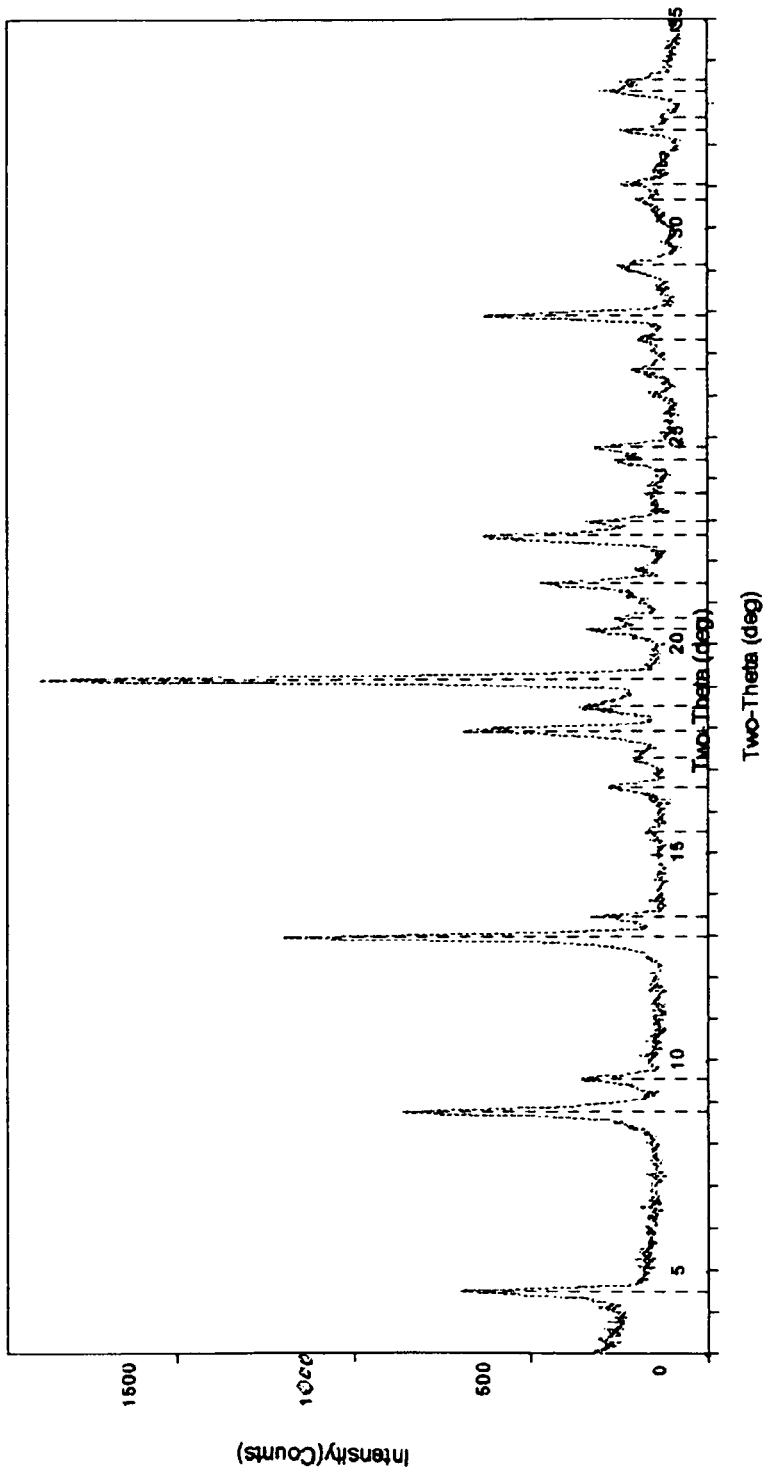
Fig. 3a: X-ray powder diffraction diagram of anhydrous form A of Example 2

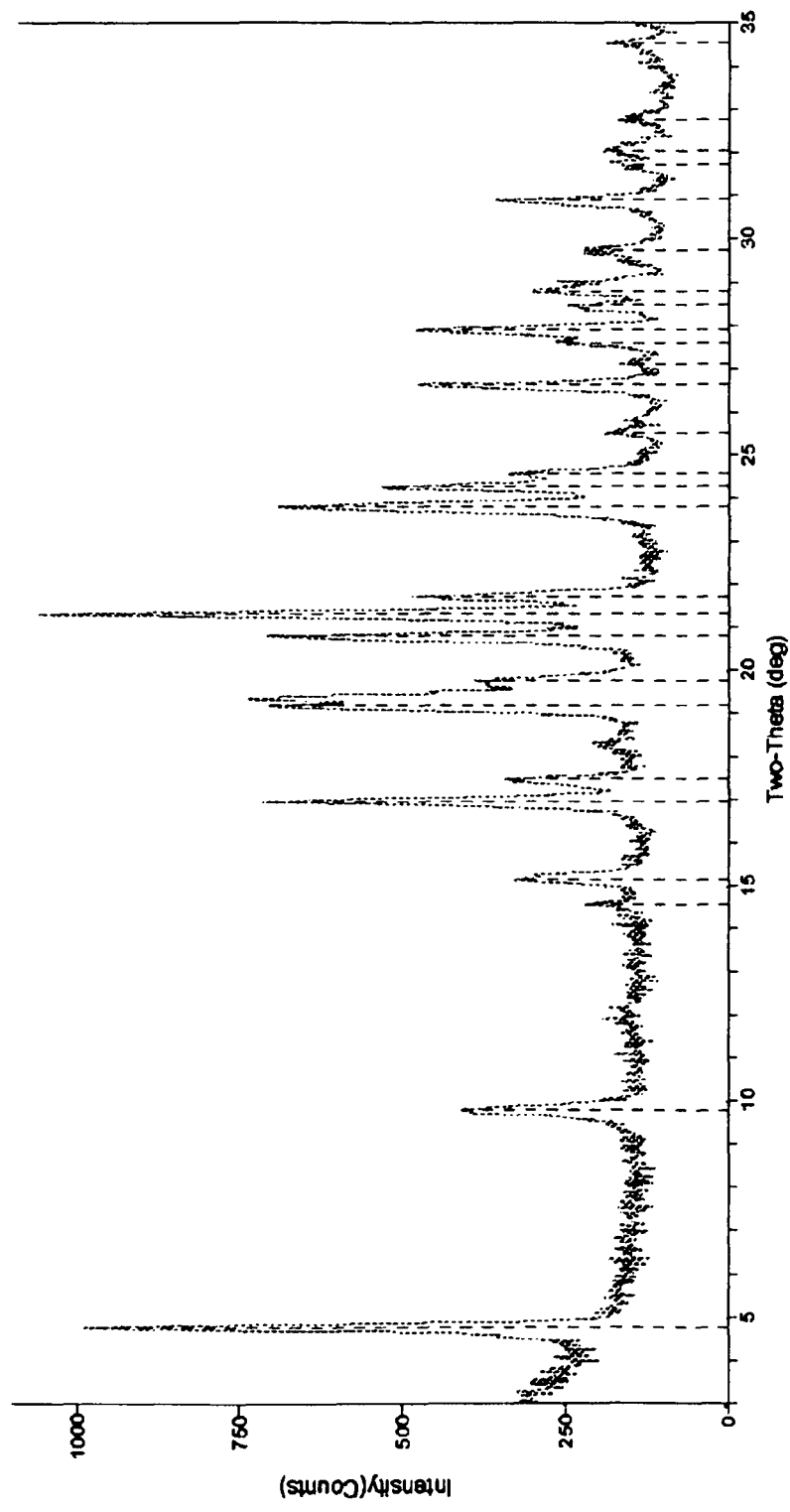
Fig. 3b: X-ray powder diffraction diagram of anhydrous form B of Example 2

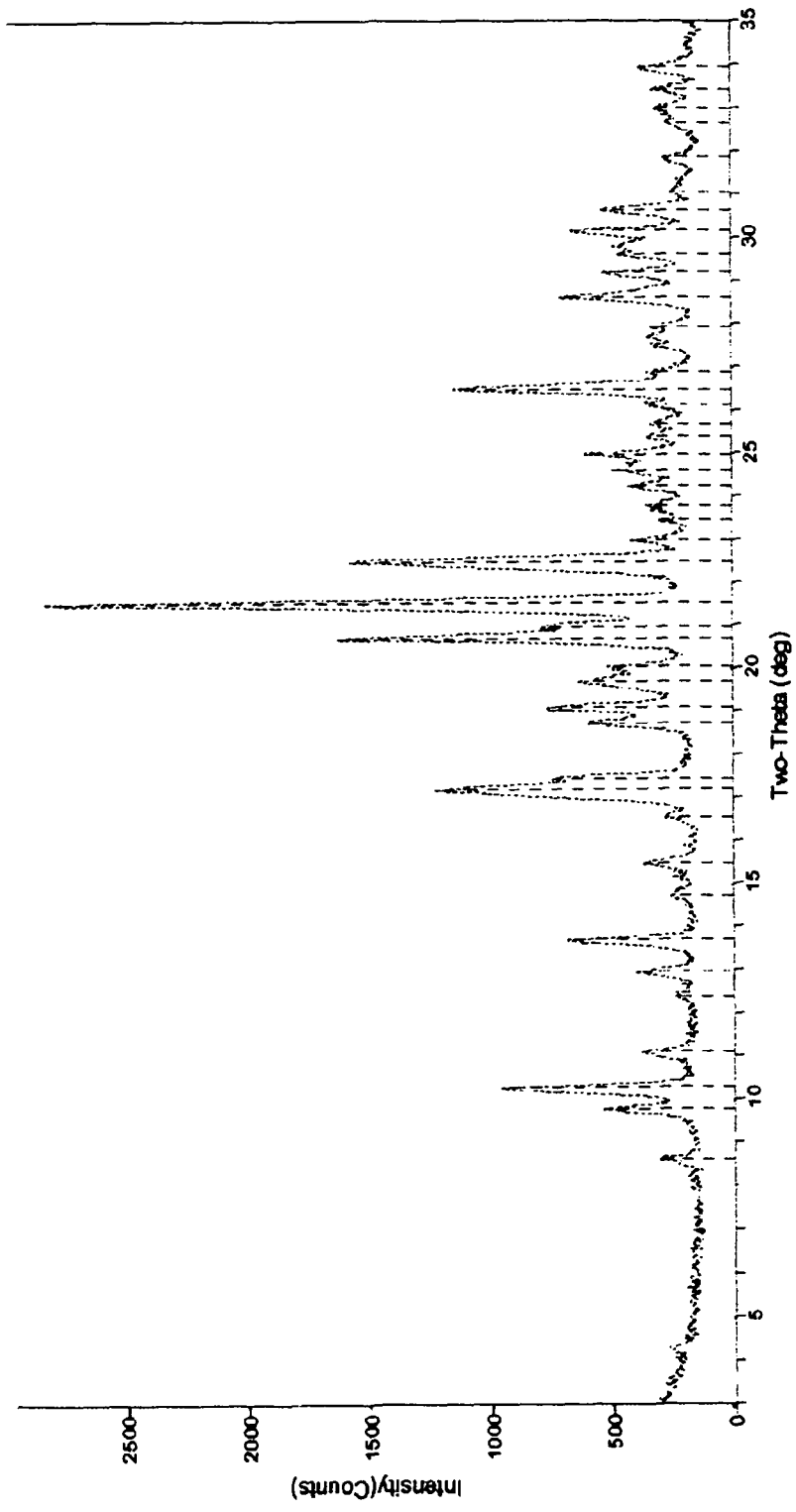
Fig. 3c: X-ray powder diffraction diagram of dihydrate form C of Example 2

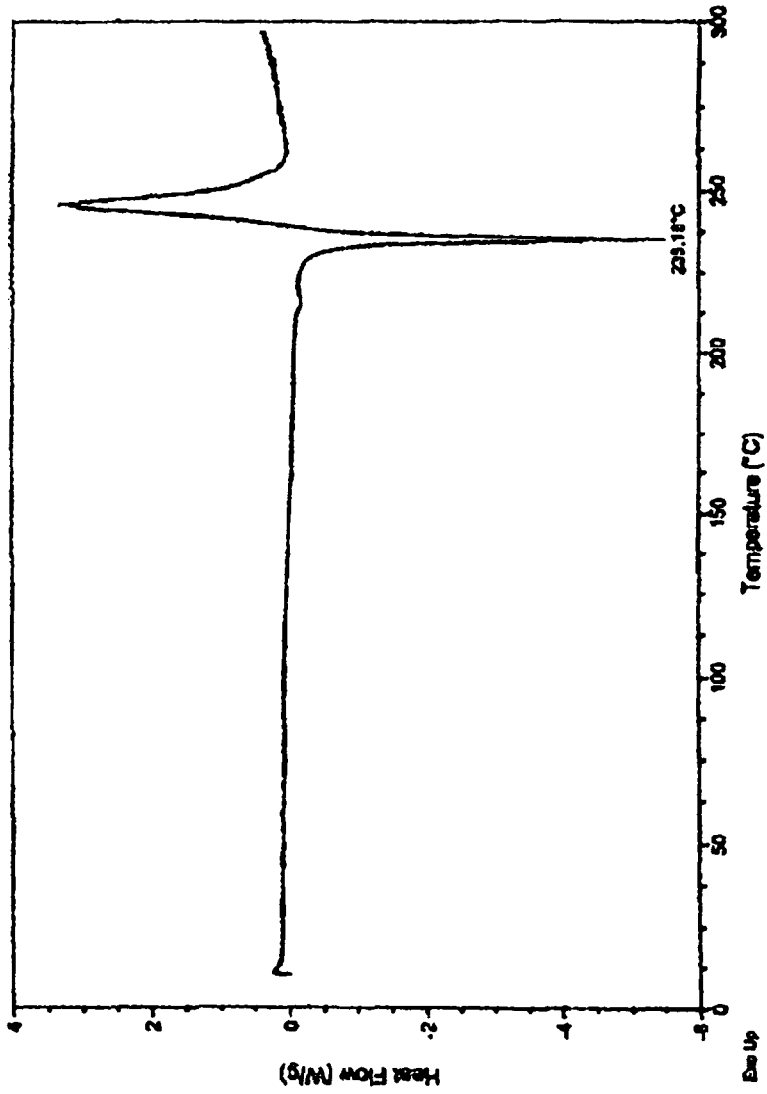
Fig. 4a: Differential Scanning Calorimetry (DSC) of the anhydrous Form A of Example 2

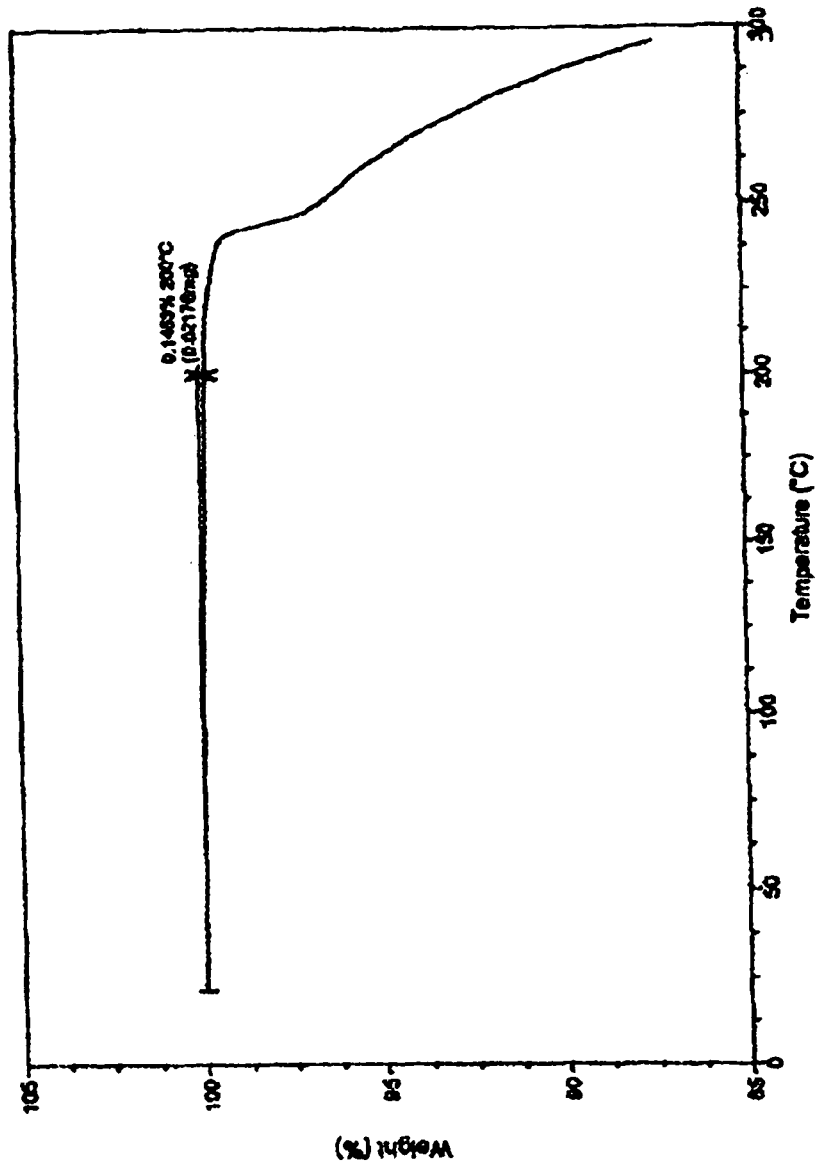
Fig. 4b: Thermogravimetric Analysis (TGA) of the anhydrous Form A of Example 2

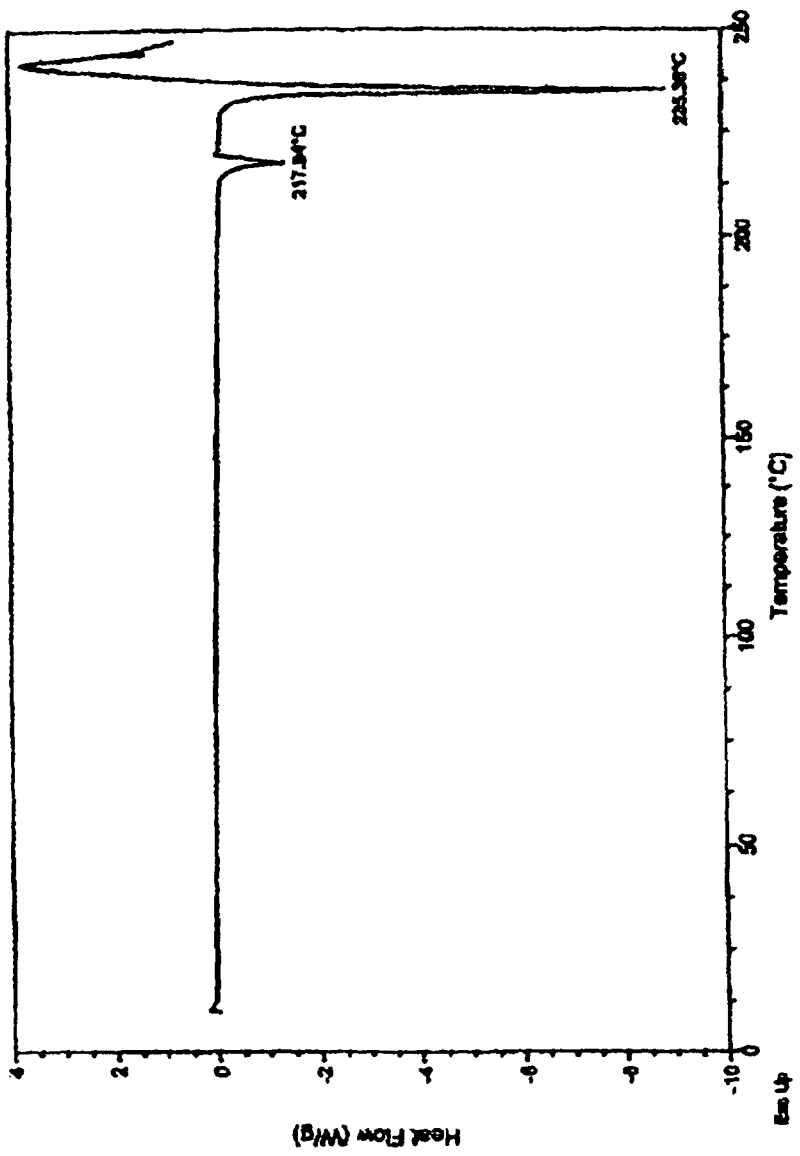
Fig. 5a: Differential Scanning Calorimetry (DSC) of the anhydrous Form B of Example 2

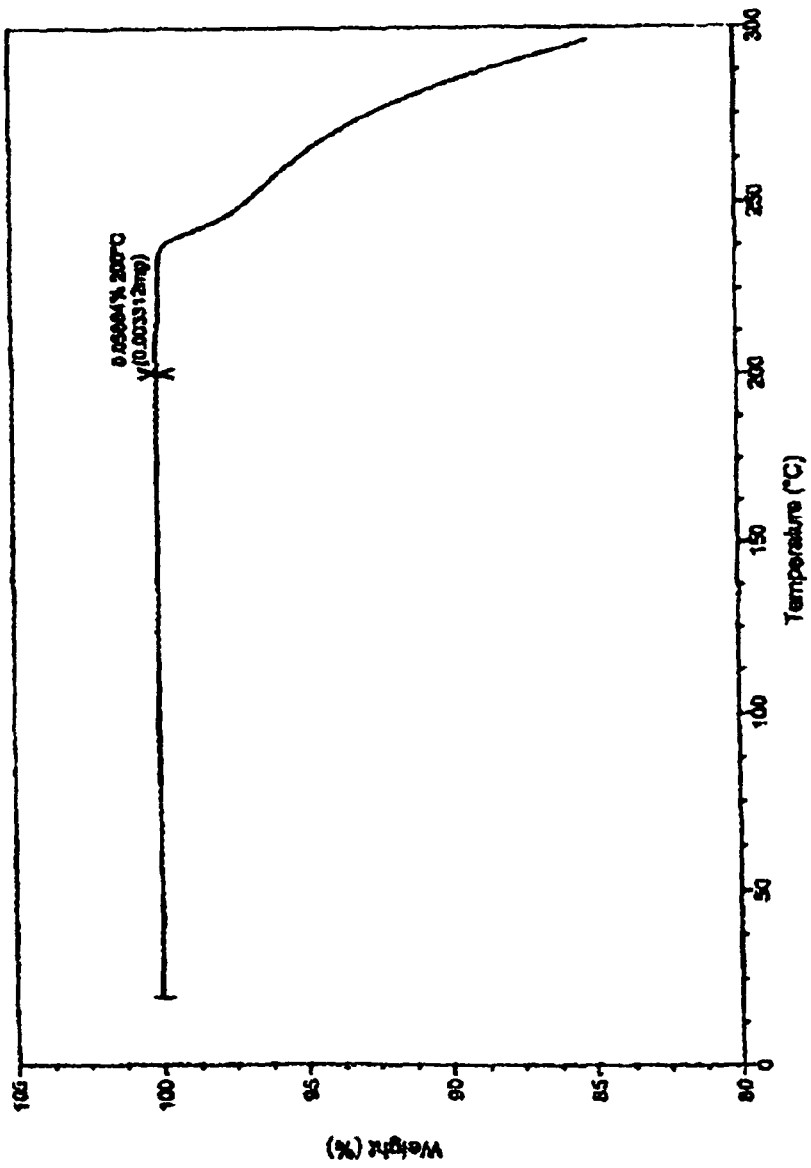
Fig. 5b: Thermogravimetric Analysis (TGA) of the anhydrous Form B of Example 2

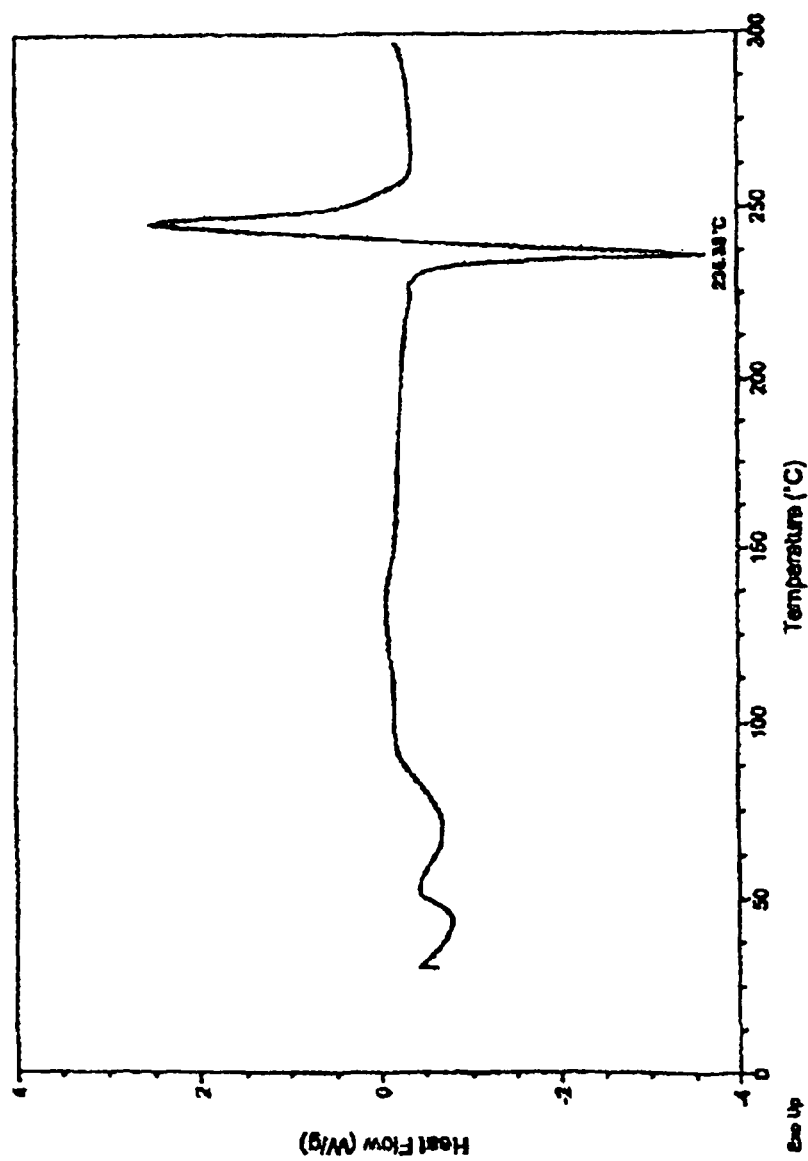

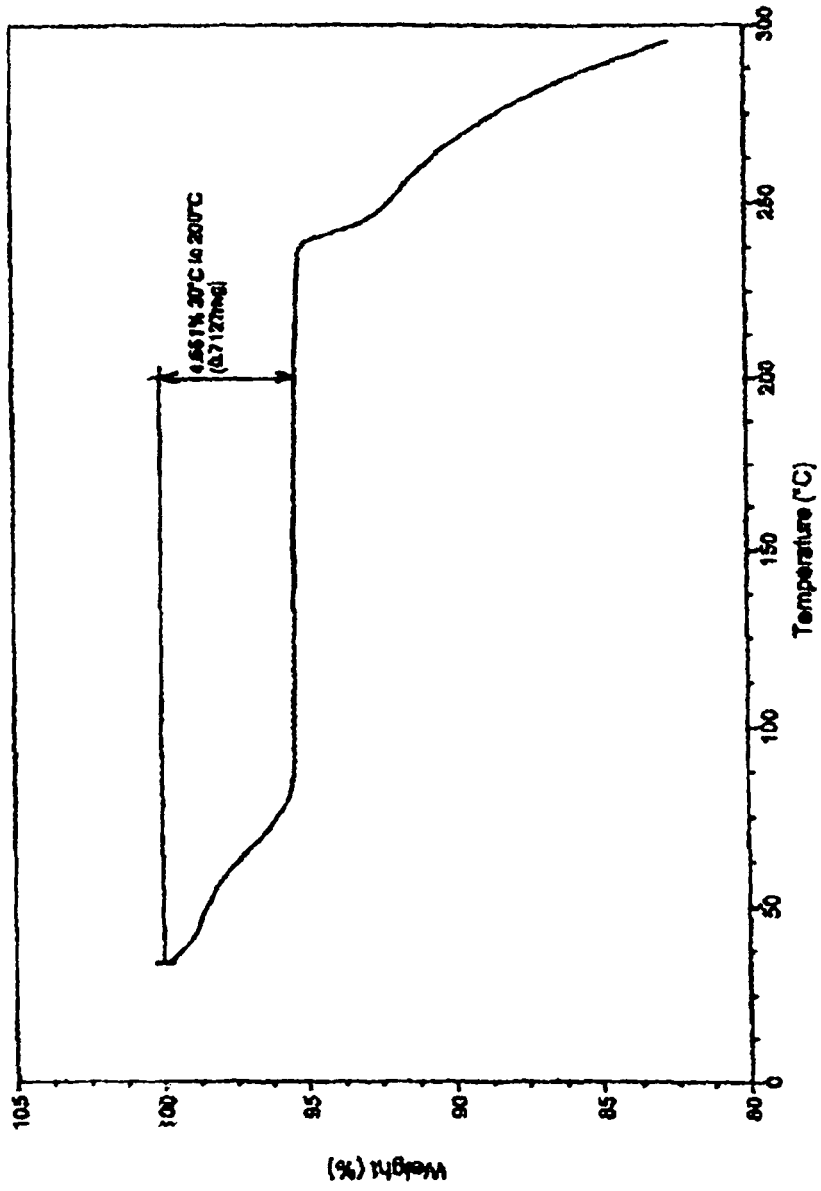
Fig. 6b: Thermogravimetric Analysis (TGA) of the dihydrate form C of Example 2

PIPERIDINO-DIHYDROTHIENOPYRIMIDINE SULFOXIDES AND THEIR USE FOR TREATING COPD AND ASTHMA

The invention relates to novel piperidino-dihydrothienopyrimidine sulfoxides of formula I,

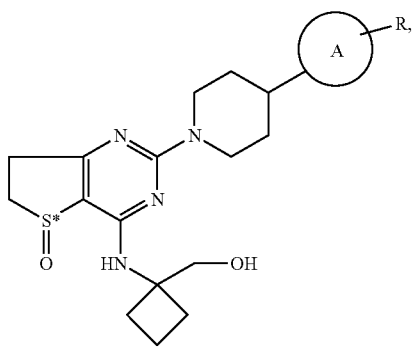

wherein Ring A is a 6-membered aromatic ring which may optionally comprise one or two nitrogen atoms and wherein R is Cl and wherein R may be located either in the para-, meta- or ortho-position of Ring A, wherein S* is a sulphur atom that represents a chiral center, and all pharmaceutically acceptable salts, enantiomers and racemates, hydrates and solvates thereof and the use of these compounds for the treatment of inflammatory or allergic diseases of the respiratory tract such as COPD or asthma.

1 PRIOR ART

WO 2006/111549 and WO 2007/118793 each disclose dihydrothieno-pyrimidinesulfoxides which are substituted by piperazine instead of piperidine. WO 2009/050248 discloses piperidino-dihydrothienopyrimidines which differ from the compounds of the invention in their substitution pattern. Due to their particular substitution pattern the compounds of the invention are at the same time more potent PDE4 inhibitors than the compounds disclosed in WO 2009/050248 and show a minimized potential for the development of unwanted gastrointestinal side effects.

2 DESCRIPTION OF THE INVENTION

Surprisingly it has been found that the compounds of the invention are due to their particular substitution pattern particularly suitable for the treatment of inflammatory disease. The compounds of the invention are further superior to the corresponding piperazino-dihydrothienopyrimidine sulfoxides of the prior art document WO 2009/050248.

The present invention therefore relates to compounds of formula I

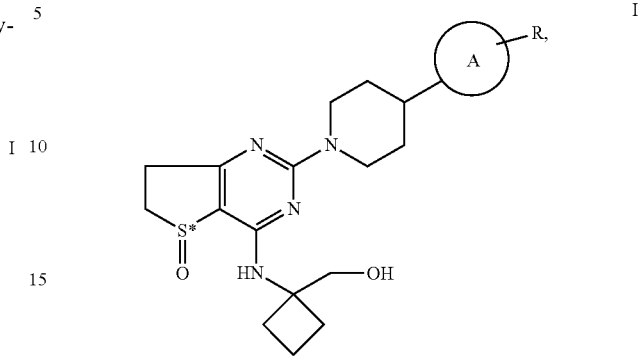

wherein Ring A is a 6-membered aromatic ring which may optionally comprise one or two nitrogen atoms and
wherein R is Cl and
wherein R may be located either in the para-, meta- or ortho-position of Ring A,
wherein S* represents a sulphur atom that is a chiral center, and all pharmaceutically acceptable salts thereof, enantiomers and racemates thereof, hydrates, solvates and polymorphs thereof.

The invention further relates to the above-mentioned compounds of formula I, wherein R is Cl and wherein R is preferably located in the para-position of Ring A, and all pharmaceutically acceptable salts thereof, enantiomers and racemates thereof, hydrates, solvates and polymorphs thereof.

The invention further relates to the above-mentioned compounds of formula I, wherein Ring A is selected from the group consisting of phenyl, pyridinyl and pyrimidinyl, and all pharmaceutically acceptable salts thereof, enantiomers and racemates thereof, hydrates, solvates and polymorphs thereof. The invention preferably relates to the above-mentioned compounds of formula I, wherein Ring A is selected from the group consisting of phenyl, pyridinyl and pyrimidinyl and wherein R is a Cl-substituent in the para-position, and all pharmaceutically acceptable salts thereof, enantiomers and racemates thereof, hydrates, solvates and polymorphs thereof.

In particular the invention concerns the compound of formula II,

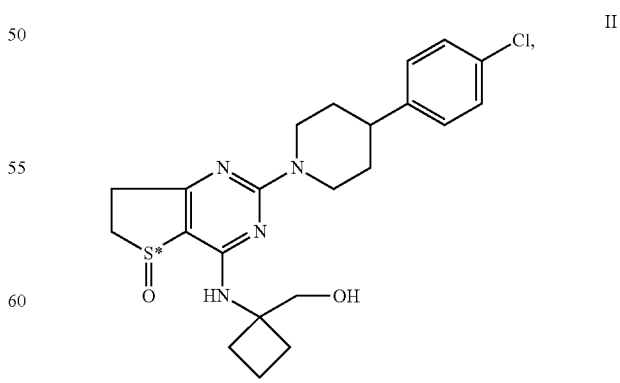

and all pharmaceutically acceptable salts thereof, enantiomers and racemates thereof, hydrates, solvates and polymorphs thereof.

In particular the invention concerns the compound of formula III,

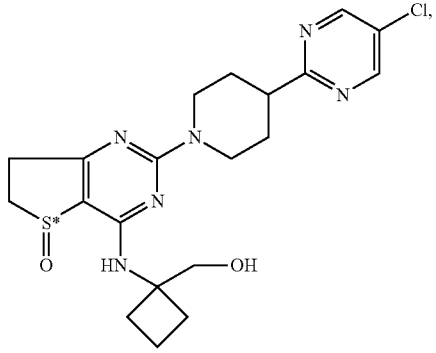

and all pharmaceutically acceptable salts thereof, enantiomers and racemates thereof, hydrates, solvates and polymorphs thereof.

The invention further relates to the above-mentioned compounds according of one of formula I, II or III, wherein S* represents a sulphur atom which represents a chiral center being in the R-configuration.

The invention further relates to the above-mentioned compounds according of one of formula I, II or III, wherein S* represents a sulphur atom which represents a chiral center being in the S-configuration.

For the compound of formula III three different polymorphs, two different anhydrous forms and one dihydrate form have been identified and characterized by X-ray powder diffraction (XRPD), by thermogravimetric analysis (TGA) and by differential scanning calorimetry (DSC).

FIG. 3a shows the X-ray powder diffraction diagram of the anhydrous form A of formula III (see Example 2). In this XRPD diagram of the anhydrous form A of formula III the following the 2•-values and d-values could be observed (Table 1).

TABLE 1

| All observable peaks for the anhydrate Form A: | | |
|---|---|---|
| 2-Theta | d(Å) | I/Io |
| 4.48 | 19.70 | 27 |
| 8.76 | 10.09 | 46 |
| 9.54 | 9.26 | 11 |
| 12.98 | 6.82 | 69 |
| 13.44 | 6.58 | 9 |
| 15.50 | 5.71 | 2 |
| 16.56 | 5.35 | 8 |
| 17.94 | 4.94 | 35 |
| 18.54 | 4.78 | 20 |
| 19.18 | 4.62 | 100 |
| 20.36 | 4.36 | 15 |
| 20.64 | 4.30 | 10 |
| 21.48 | 4.13 | 23 |
| 22.62 | 3.93 | 38 |
| 22.98 | 3.87 | 15 |
| 23.65 | 3.76 | 4 |
| 24.46 | 3.64 | 15 |
| 24.76 | 3.59 | 21 |
| 26.61 | 3.35 | 5 |
| 27.34 | 3.26 | 13 |
| 27.92 | 3.19 | 28 |
| 29.14 | 3.06 | 15 |
| 30.68 | 2.91 | 11 |
| 31.05 | 2.88 | 17 |

TABLE 1-continued

| All observable peaks for the anhydrate Form A: | | |
|---|---|---|
| 2-Theta | d(Å) | I/Io |
| 32.34 | 2.77 | 8 |
| 32.65 | 2.74 | 3 |
| 33.28 | 2.69 | 20 |
| 33.54 | 2.67 | 17 |

The major peaks of the XRPD diagram of anhydrous Form A of the compound of formula III are listed in Table 2.

TABLE 2

| Major peaks for the anhydrate Form A: | | |
|---|---|---|
| 2-Theta | d(Å) | I/Io |
| 4.48 | 19.70 | 27 |
| 8.76 | 10.09 | 46 |
| 12.98 | 6.82 | 69 |
| 17.94 | 4.94 | 35 |
| 19.18 | 4.62 | 100 |
| 21.48 | 4.13 | 23 |
| 22.62 | 3.93 | 38 |
| 24.76 | 3.59 | 21 |
| 27.92 | 3.19 | 28 |

The most prominent peaks of the XRPD diagram of anhydrous Form A of the compound of formula III are listed in Table 3.

TABLE 3

| Prominent peaks for the anhydrate Form A: | | |
|---|---|---|
| 2-Theta | d(Å) | I/Io |
| 8.76 | 10.09 | 46 |
| 12.98 | 6.82 | 69 |
| 19.18 | 4.62 | 100 |

FIG. 3b shows the X-ray powder diffraction diagram of the anhydrous form B of formula III (see Example 2). In this XRPD diagram of the anhydrous form B of formula III the following 2•-values and d-values could be observed (Table 4).

TABLE 4

| All observable peaks for the anhydrate Form B: | | |
|---|---|---|
| 2-Theta | d(Å) | I/Io |
| 4.78 | 18.47 | 46 |
| 9.78 | 9.04 | 25 |
| 14.56 | 6.08 | 5 |
| 15.14 | 5.85 | 17 |
| 16.96 | 5.22 | 43 |
| 17.48 | 5.07 | 14 |
| 19.18 | 4.62 | 100 |
| 19.74 | 4.49 | 41 |
| 20.80 | 4.27 | 38 |
| 21.30 | 4.17 | 71 |
| 21.72 | 4.09 | 28 |
| 23.82 | 3.73 | 50 |
| 24.28 | 3.66 | 55 |
| 24.58 | 3.62 | 35 |
| 25.53 | 3.49 | 4 |
| 26.64 | 3.34 | 21 |
| 27.12 | 3.29 | 2 |
| 27.61 | 3.23 | 13 |
| 27.90 | 3.20 | 31 |
| 28.48 | 3.13 | 8 |
| 28.78 | 3.10 | 18 |

TABLE 4-continued

All observable peaks for the anhydrate Form B:

| 2-Theta | d(Å) | I/Io |
|---|---|---|
| 29.74 | 3.00 | 8 |
| 30.92 | 2.89 | 18 |
| 31.75 | 2.82 | 6 |
| 32.04 | 2.79 | 10 |
| 32.78 | 2.73 | 2 |
| 34.55 | 2.59 | 8 |

The major peaks of the XRPD diagram of anhydrous Form B of the compound of formula III are listed in Table 5.

TABLE 5

Major peaks for the anhydrate Form B:

| 2-Theta | d(Å) | I/Io |
|---|---|---|
| 4.78 | 18.47 | 46 |
| 9.78 | 9.04 | 25 |
| 15.14 | 5.85 | 17 |
| 16.96 | 5.22 | 43 |
| 19.18 | 4.62 | 100 |
| 19.74 | 4.49 | 41 |
| 20.80 | 4.27 | 38 |
| 21.30 | 4.17 | 71 |
| 21.72 | 4.09 | 28 |
| 23.82 | 3.73 | 50 |
| 24.28 | 3.66 | 55 |
| 27.90 | 3.20 | 31 |

The most prominent peaks of the XRPD diagram of anhydrous Form B of the compound of formula III are listed in Table 6.

TABLE 6

Prominent peaks for the anhydrate Form B

| 2-Theta | d(Å) | I/Io |
|---|---|---|
| 4.78 | 18.47 | 46 |
| 16.96 | 5.22 | 43 |
| 19.18 | 4.62 | 100 |
| 21.30 | 4.17 | 71 |
| 24.28 | 3.66 | 55 |
| 23.82 | 3.73 | 50 |

Consequently the invention concerns a crystalline anhydrous compound of formula III which shows a reflex peak in the X-ray powder diffraction diagram with a d-value of 4.62 Å.

Further the invention concerns a crystalline anhydrous compound of formula III which shows reflex peaks in the X-ray powder diffraction diagram with d-values of 4.62 Å, 6.82 Å and 10.09 Å.

Further the invention concerns a crystalline anhydrous compound of formula III, which shows reflex peaks in the X-ray powder diffraction diagram with d-values of 4.62 Å, 4.17 Å and 3.66 Å.

Additionally the invention relates to a crystalline anhydrous compound of formula III, which shows reflex peaks in the X-ray powder diffraction diagram with d-values of 4.62 Å, 6.82 Å, 10.09 Å, 3.93 Å and 4.94 Å.

Additionally the invention relates to a crystalline anhydrous compound of formula III, which shows reflex peaks in the X-ray powder diffraction diagram with d-values of 4.62 Å, 4.17 Å, 3.66 Å, 3.73 Å and 18.47 Å.

FIG. 3c shows the X-ray powder diffraction diagram of the dihydrate form C of formula III (see Example 2). In this XRPD diagram of the dihydrate form C of formula III the following 2•-values and d-values could be observed (Table 7).

TABLE 7

All observable peaks for the dihydrate Form C:

| 2-Theta | d(Å) | I/Io |
|---|---|---|
| 8.60 | 10.27 | 4 |
| 9.78 | 9.04 | 15 |
| 10.28 | 8.60 | 28 |
| 11.10 | 7.97 | 6 |
| 12.96 | 6.83 | 8 |
| 13.72 | 6.45 | 16 |
| 14.72 | 6.01 | 5 |
| 15.46 | 5.73 | 9 |
| 17.20 | 5.15 | 70 |
| 18.72 | 4.74 | 21 |
| 19.10 | 4.64 | 29 |
| 19.70 | 4.50 | 33 |
| 20.04 | 4.43 | 26 |
| 20.70 | 4.29 | 75 |
| 21.54 | 4.12 | 100 |
| 22.48 | 3.95 | 61 |
| 23.00 | 3.86 | 5 |
| 23.78 | 3.74 | 5 |
| 24.26 | 3.67 | 7 |
| 24.62 | 3.61 | 15 |
| 24.98 | 3.56 | 19 |
| 26.50 | 3.36 | 41 |
| 27.92 | 3.19 | 8 |
| 28.62 | 3.12 | 20 |
| 29.21 | 3.05 | 9 |
| 29.64 | 3.01 | 15 |
| 30.18 | 2.96 | 19 |
| 30.66 | 2.91 | 16 |
| 31.88 | 2.80 | 4 |
| 33.00 | 2.71 | 12 |
| 33.94 | 2.64 | 9 |

The major peaks of the XRPD diagram of dihydrate Form C of the compound of formula III are listed in Table 8.

TABLE 8

Major peaks for the dihydrate Form C:

| 2-Theta | d(Å) | I/Io |
|---|---|---|
| 10.28 | 8.60 | 28 |
| 17.20 | 5.15 | 70 |
| 18.72 | 4.74 | 21 |
| 19.10 | 4.64 | 29 |
| 19.70 | 4.50 | 33 |
| 20.04 | 4.43 | 26 |
| 20.70 | 4.29 | 75 |
| 21.54 | 4.12 | 100 |
| 22.48 | 3.95 | 61 |
| 26.50 | 3.36 | 41 |
| 28.62 | 3.12 | 20 |

The most prominent peaks of the XRPD diagram of dihydrate Form C of the compound of formula III are listed in Table 9.

TABLE 9

Prominent peaks for the dihydrate Form C:

| 2-Theta | d(Å) | I/Io |
|---|---|---|
| 17.20 | 5.15 | 70 |
| 20.70 | 4.29 | 75 |
| 21.54 | 4.12 | 100 |
| 22.48 | 3.95 | 61 |
| 26.50 | 3.36 | 41 |

Consequently, the invention relates to a crystalline dihydrate compound of formula III, which shows a reflex peak in the X-ray powder diffraction diagram with a d-value of 4.12 Å.

The invention also relates to a crystalline dihydrate compound of formula III, which shows reflex peaks in the X-ray powder diffraction diagram with d-values of 4.12 Å, 4.29 Å and 5.15 Å.

The invention further relates to a crystalline dihydrate compound of formula III, which shows reflex peaks in the X-ray powder diffraction diagram with d-values of 4.12 Å, 4.29 Å, 5.15 Å, 3.95 Å and 3.36 Å.

In another aspect the invention relates to the above-mentioned compounds for use as a medicament.

Another aspect of the invention concerns a method of treating a disease which can be treated by the inhibition of the PDE4-enzyme comprising the step of administering one of the aforementioned compounds according to at least one of formulas I, II or III to a patient in need thereof.

Further the invention concerns the use of one of the aforementioned compounds according to at least one of formulas I, II or III for preparing a medicament for the treatment and/or prevention of a disease which can be treated by the inhibition of the PDE4-enzyme.

Further the invention concerns one of the aforementioned compounds according to at least one of formulas I, II or III for the treatment and/or prevention of a disease which can be treated by the inhibition of the PDE4-enzyme.

The invention further relates to the above-mentioned method of treating a disease which can be treated by the inhibition of the PDE4-enzyme comprising the step of administering one of the aforementioned compounds according to at least one of formulas I, II or III to a patient in need thereof, characterised in that the disease to be treated is selected from the group consisting of a respiratory disease, a gastrointestinal disease, an inflammatory disease of the joints, the skin or the eyes, cancer and a disease of the peripheral or central nervous system.

Further the invention concerns the use of one of the aforementioned compounds according to at least one of formulas I, II or III for preparing a medicament for the treatment and/or prevention of a disease which can be treated by the inhibition of the PDE4-enzyme, wherein the disease to be treated is selected from the group consisting of a respiratory disease, a gastrointestinal disease, an inflammatory disease of the joints, the skin or the eyes, cancer and a disease of the peripheral or central nervous system.

Further the invention concerns one of the aforementioned compounds according to at least one of formulas I, II or III for the treatment and/or prevention of a disease which can be treated by the inhibition of the PDE4-enzyme, wherein the disease to be treated is selected from the group consisting of a respiratory disease, a gastrointestinal disease, an inflammatory disease of the joints, the skin or the eyes, cancer and a disease of the peripheral or central nervous system.

The invention further relates to the above-mentioned method of treating a disease which is selected from the group consisting of a respiratory or pulmonary disease which is accompanied by increased mucus production, inflammations and/or obstructive diseases of the respiratory tract, comprising the step of administering one of the aforementioned compounds according to at least one of formulas I, II or III to a patient in need thereof.

Further the invention concerns the use of one of the aforementioned compounds according to at least one of formulas I, II or III for preparing a medicament for the treatment and/or prevention of a disease selected from the group consisting of a respiratory or pulmonary disease which is accompanied by increased mucus production, inflammations and/or obstructive diseases of the respiratory tract, comprising the step of administering one of the aforementioned compounds according to at least one of formulas I, II or III to a patient in need thereof.

Further the invention concerns one of the aforementioned compounds according to at least one of formulas I, II or III for the treatment and/or prevention of a disease selected from the group consisting of a respiratory or pulmonary disease which is accompanied by increased mucus production, inflammations and/or obstructive diseases of the respiratory tract, comprising the step of administering one of the aforementioned compounds according to at least one of formulas I, II or II.

The invention further relates to the above-mentioned method of treating a disease which is selected from the group consisting of COPD, chronic sinusitis, idiopathic pulmonary fibrosis, alpha 1 antitrypsin deficiency, asthma and chronic bronchitis, comprising the step of administering one of the aforementioned compounds according to at least one of formulas I, II or III to a patient in need thereof.

Further the invention concerns the use of one of the aforementioned compounds according to at least one of formulas I, II or III for preparing a medicament for the treatment and/or prevention of a disease selected from the group consisting of COPD, chronic sinusitis, idiopathic pulmonary fibrosis, alpha 1 antitrypsin deficiency, asthma and chronic bronchitis.

Further the invention concerns one of the aforementioned compounds according to at least one of formulas I, II or III for the treatment and/or prevention of a disease selected from the group consisting of COPD, chronic sinusitis, idiopathic pulmonary fibrosis, alpha 1 antitrypsin deficiency, asthma and chronic bronchitis.

Further the invention concerns the use of one of the aforementioned compounds according to at least one of formulas I, II or III for preparing a medicament for the treatment and/or prevention of a disease selected from the group consisting of rheumatoid arthritis, sarcoidosis, glaucoma and the dry eyes syndrome.

Further the invention concerns one of the aforementioned compounds according to at least one of formulas I, II or III for the treatment and/or prevention of a disease selected from the group consisting of rheumatoid arthritis, sarcoidosis, glaucoma and the dry eyes syndrome.

The invention further relates to the above-mentioned method of treating a disease which is selected from the group consisting of Crohn's disease and ulcerative colitis, comprising the step of administering one of the aforementioned compounds according to at least one of formulas I, II or III to a patient in need thereof.

Further the invention concerns the use of one of the aforementioned compounds according to at least one of formulas I, II or III for preparing a medicament for the treatment and/or prevention of a disease selected from the group consisting of Crohn's disease and ulcerative colitis.

Further the invention concerns one of the aforementioned compounds according to at least one of formulas I, II or III for the treatment and/or prevention of a disease selected from the group consisting of Crohn's disease and ulcerative colitis.

The invention further relates to the above-mentioned method of treating a disease which is selected from the group consisting of depression, bipolar or manic depression, acute and chronic anxiety states, schizophrenia, Alzheimer's disease, Parkinson's disease, acute and chronic multiple sclerosis or acute and chronic pain and brain damage caused by stroke, hypoxia or cranio-cerebral trauma, comprising the step of administering one of the aforementioned compounds according to at least one of formulas I, II or III to a patient in need thereof.

Further the invention concerns the use of one of the aforementioned compounds according to at least one of formulas I, II or III for preparing a medicament for the treatment and/or prevention of a disease selected from the group consisting of depression, bipolar or manic depression, acute and chronic anxiety states, schizophrenia, Alzheimer's disease, Parkinson's disease, acute and chronic multiple sclerosis or acute and chronic pain and brain damage caused by stroke, hypoxia or cranio-cerebral trauma.

Further the invention concerns one of the aforementioned compounds according to at least one of formulas I, II or III for the treatment and/or prevention of a disease selected from the group consisting of depression, bipolar or manic depression, acute and chronic anxiety states, schizophrenia, Alzheimer's disease, Parkinson's disease, acute and chronic multiple sclerosis or acute and chronic pain and brain damage caused by stroke, hypoxia or cranio-cerebral trauma.

In another aspect the invention concerns a pharmaceutical composition comprising at least one of the aforementioned compounds according to at least one of formulas I, II or III.

In a further aspect the invention relates to a pharmaceutical composition characterised in that it contains at least one of the aforementioned compounds of at least one of formulas I, II or III in combination with one or more active substances selected from the group consisting of betamimetics, corticosteroids, anticholinergics, other PDE4 inhibitors, NSAIDS, COX2 inhibitors, EP4 receptor antagonists, EGFR-inhibitors, LTD4-antagonists, CCR3-inhibitors, iNOS-inhibitors, MRP4-inhibitors and SYK inhibitors.

In another aspect the invention relates to a method of manufacturing the compound A

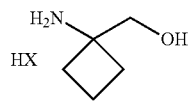

wherein HX is a pharmaceutically acceptable acid,
comprising the steps a) and b), wherein in
step a) compound B

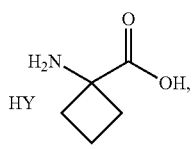

wherein HY is a pharmaceutically acceptable acid,
is reduced by borane and wherein in
step b) a pharmaceutically acceptable acid HX is added in order to obtain compound A.

In one embodiment of the above-mentioned method of manufacturing compound A the borane for the reduction in step a) is added directly.

In another embodiment of the above-mentioned method of manufacturing compound A the borane for the reduction in step a) is generated in-situ.

In a preferred embodiment of the above-mentioned method of manufacturing compound A the borane for the reduction in step a) is generated in situ either from the combination of $NaBH_4$ and $I_2$ or from the combination of $NaBH_4$ and $BF_3$—$OEt_2$.

In another preferred embodiment of the above-mentioned method of one of manufacturing compound A the acid HX is selected from tosylic acid or hydrochloric acid.

In a further embodiment of the above-mentioned method of one of manufacturing compound A the pharmaceutically acceptable acid HY in compound B is HCl.

In another aspect the invention relates to a method of manufacturing compound C

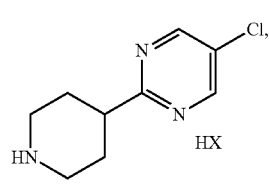

wherein HX is tosylic acid, hydrochloric acid or sulphuric acid, comprising the steps i), ii) and iii), wherein in step i) 4-cyano-piperidine is contacted first with an acid and is then reacted with ammonia in order to obtain intermediate E

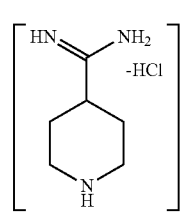

and wherein in step ii) intermediate E is reacted with compound D in the presence of a base

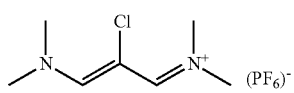

and wherein in step iii) the acid HX is added.

In a preferred embodiment of the above-mentioned method of manufacturing compound C 4-cyano-piperidine is contacted with hydrochloric acid and is then reacted with ammonia in order to obtain intermediate E in step i).

In a preferred embodiment of the above-mentioned method of manufacturing compound C the intermediate E is reacted with compound D in the presence of sodium methanolate in step ii).

In a further aspect the invention relates to intermediates of formula VIII

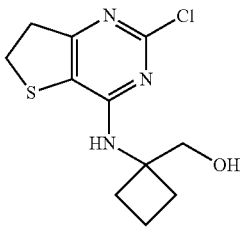

VIII and their salts.

In a further aspect the invention relates to intermediates of formula IX

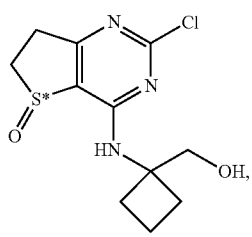

IX and their salts,
wherein S* stands for a sulphur atom that represents a chiral center.

Compounds of the general formulas I, II und III contain basic groups. Therefore compounds of the general formulas I, II und III may form salts with pharmaceutically acceptable inorganic acids such as hydrochloric acid, sulphuric acid, phosphoric acid, sulphonic acid or with organic acids (such as for instance maleic acid, fumaric acid, citric acid, tartaric acid or acetic acid).

As described above the compounds of formulas I, II and III may be transformed into their pharmacologically acceptable salts for their use as pharmaceutics. For instance these compounds may form physiologically and pharmacologically acceptable acid addition salts with inorganic or with organic acids. In order to produce these acid addition salts of the compounds of formulas I, II and III for instance hydrochloric acid, hydrobromic acid, sulphuric acid, phosphoric acid, methyl sulphonic acid, acetic acid, fumaric acid, succinic acid, lactic acid, citric acid, tartaric acid and maleic acid may be used. Further it is possible to use mixtures of the aforementioned acids.

The compounds of formulas I, II and III may also be present in the form of their individual optic isomers or enantiomers, in mixtures of the individual enantiomers or in the form of their racemates, and in the form of their free bases or in the form of their acid addition salts with pharmacologically acceptable acids (for instance acid addition salts with hydrohalogenic acids such as hydrochloric acid or hydrobromic acid or with organic acids such as oxalic acid, fumaric acid, diglycolic acid or methyl sulfonic acid.

The compounds of the invention may also be present in their racemic forms, but may also be present in the form of one pure enantiomers, that means in their (R)- or in their (S)-forms.

As mentioned before the pharmacologically acceptable salts of the compounds of formula I, II and III are also a preferred aspect of the instant invention. These pharmaceutically acceptable salts of the compounds of formulas I, II and III may also be present in the form of their hydrates (for instance mono- or dihydrates) and/or in the form of their solvates.

A solvate of a compound of formula I, II or III is defined herein as a crystalline salt of the respective compound of formula I, II or III which contains solvent molecules (for instance ethanol, methanol etc.) within its crystal lattice.

A hydrate of a compound of formula I, II or III is defined herein as a crystalline salt of a compound of formula I, II or III which contains crystalline water in its crystal lattice.

3 METHODS OF SYNTHESIS

Generation of Examples 1 and 2

Scheme 1:

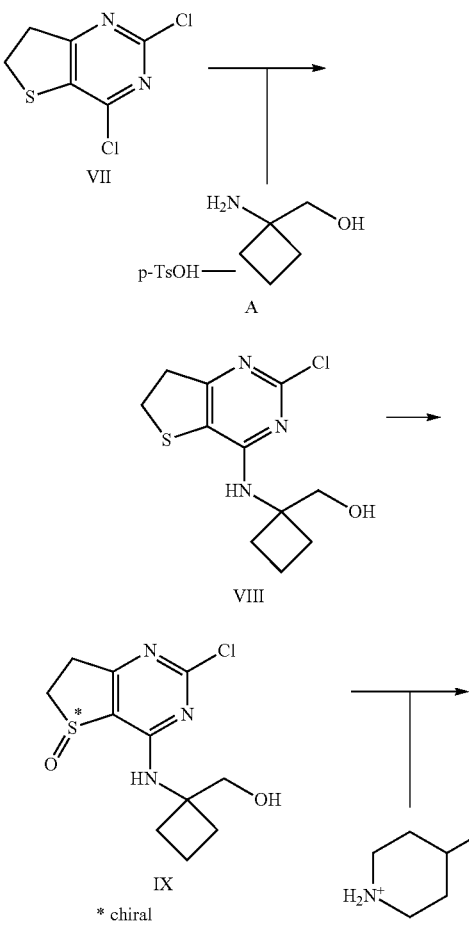

X⁻ = Cl⁻ or Ts⁻ or HSO₄⁻
C: R = 4-Chlorophenyl
G: R = 5-Chloropyrimidine-2-yl

13

-continued

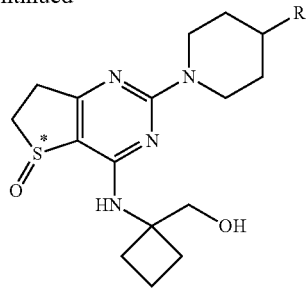

Example 1
R = 4-chlorophenyl; or
Example 2
R = 5-chloropyrimidine-2-yl 3.1. Generation of Compound VII

14 organic layer was collected and washed with water (251 ml). The mixture was concentrated to a minimum volume by distillation under reduced pressure at 50° C. Dichloromethane (251 ml) was charged and the mixture was again concentrated under reduced pressure by distillation at 40-45° C. Crude product III (480 g) was used in the next step without further purification.

3.1.2 Synthesis of Methyl-3-oxo-tetrahydrothiophene-2-carboxylate (Compound IV)

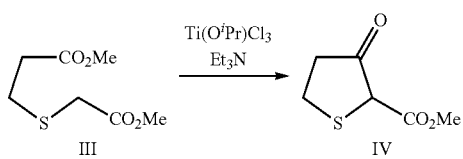

Scheme 2

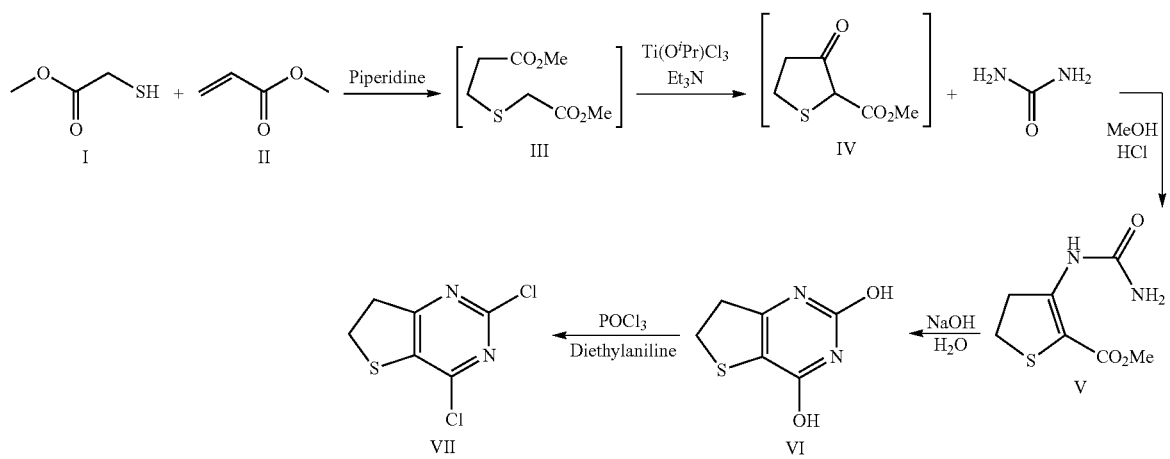

3.1.1 Synthesis of Dimethyl-3-thiaadipate (Compound III)

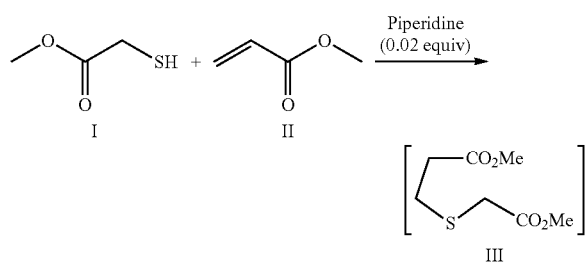

Methyl thioglycolate (292 g, 2.61 mol) and piperidine (4.43 g, 0.052 mol) were charged to an inerted jacketed reactor equipped with an addition funnel, mechanical stirrer, $N_2$ line and thermocouple thermometer. Methyl acrylate (250 g, 2.87 mol) was then added slowly over a period of 30 min keeping the temperature at approximately 45° C. Upon complete addition, the mixture was stirred at 45° C. for 30 min Piperidine (17.9 g, 210 mmol) was added and stirring at 45° C. continued for 30 min (in order to scavenge of excess acrylate). Tert-butylmethylether (MTBE) (251 ml) was charged, the mixture was cooled to 15° C. and 1 M HCl (251 ml) was added. The mixture was stirred for 5 min and the $TiCl_4$ (1.0 M $CH_2Cl_2$, 1.16 L; 1.16 mol) was charged to an inerted and dried jacketed reactor equipped with temperature probe, mechanical stirrer and a dropping funnel. The reactor contents were cooled to −10° C. and isopropanol (89.6 ml, 1.16 mol) was charged at or below −10° C. The mixture was stirred at −10° C. for 30 min and dimethyl 3-thiaadipate (200 g, 1.01 mol) was charged slowly over 1 h keeping the internal temperature at or below −10° C. The reaction was stirred for an additional 30 min at −10° C. and $Et_3N$ (489 mL, 3.49 mol) was slowly charged over 1.5 hours keeping the internal temperature at or below −10° C. The mixture was stirred at or below −10° C. for 1.5 hours. 3 N HCl (1.01 L; 3.03 mol) was slowly charged keeping the internal temperature below 10° C. The temperature was increased to 30° C. and the mixture was stirred for 1 hour. The mixture was allowed to settle, the organic layer was collected and the aqueous layer was extracted with dichloromethane twice (1.5 l per extraction). The combined organic portions were washed twice with water (1.5 l per wash) and dried with $MgSO_4$ (40 g). The resulting solution was concentrated to a minimum volume under reduced pressure at 25-35° C. to afford crude IV (148.6 g). The spectral data of IV is consistent with literature values (Liu, H.-J.; Teng, K. N. *Can. J. Chem.* 1982, 60, 437).

3.1.3 Synthesis of 3-Ureido-4,5-dihydro-thiophene-2-carboxylic acid methyl ester (Compound V)

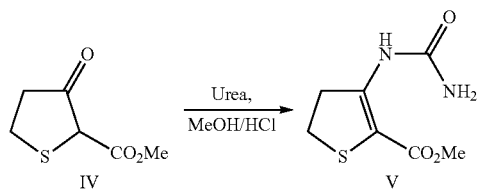

Urea (2.16 kg, 35.9 mol) was charged into a dry, jacketed reactor equipped with a stirrer, $N_2$ line and thermocouple thermometer. 3-oxo-tetrahydro-thiophene-2-carboxylic acid methyl ester (Compound IV, 3.0 kg) was charged followed by methanol (4.5 l). Conc. HCl (297 ml, 3.59 mol) was charged at 20-25° C. and the mixture stirred at reflux for 4-6 hours. The reaction mixture was cooled to 0° C. and the resulting solid was collected by filtration. The cake was washed with water twice (2 l water per wash) and dried in a vacuum oven at 50° C. to afford 4.17 kg (83% w/w) of compound V (95% yield), $^1$H NMR (500 MHz, $(CD_3)_2SO$).3.10 (dd, 2H, J=8.5, 8.5 Hz), 3.50 (dd, 2H, J=8.5, 8.5 Hz), 3.73 (s, 3H), 6.50-7.20 (bs, 2H), 9.47 (s, 1H); $^{13}$C NMR (125 MHz, $(CD_3)_2SO$) • 28.7, 37.8, 52.4, 100.0, 151.6, 154.7, 165.7; LCMS (EI) for $C_7H_{11}N_2O_3S$, (M+H)+ calcd. 203.0, measd. 203.0.

3.1.4 Synthesis of 6,7-Dihydro-thieno[3,2-d]pyrimidine-2,4-diol (Compound VI)

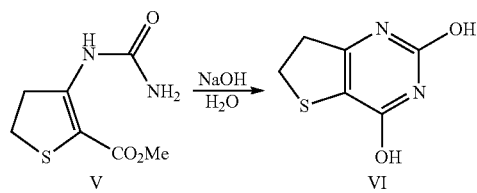

Compound V (2.0 kg, 9.47 mol) was added to a solution of water (6.0 l) and NaOH (379 g, 9.47 mol) at normal room temperature. The above mixture was stirred at 85° C. for 3 hours. After cooling to 0° C., conc. HCl (861 ml, 10.4 mol) was added slowly until the pH of the solution was 0-1. The mixture was cooled to 0° C., stirred for 5-10 min and the resulting solid was collected by filtration. The cake was washed thoroughly with water twice (1 l per rinse), air-dried for 2-3 hours (suction) and then dried further in a vacuum oven at 50° C. for 12-16 hours to afford 1.67 kg of compound VI. $^1$H NMR (500 MHz, $(CD_3)_2SO$) • 3.11 (dd, 2H, J=8.5, 8.5 Hz), 3.31 (dd, 2H, J=8.5, 8.5 Hz), 11.14 (s, 1H), 11.38 (s, 1H); $^{13}$C NMR (125 MHz, $(CD_3)_2SO$) • 29.3, 35.4, 108.5, 150.5, 152.4, 160.4; LCMS (EI) for $C_6H_7N_2O_2S$, (M+H)+ calcd. 171.0, measd. 171.0.

3.1.5 Synthesis of 2.4-dichloro-thieno[3,2-d]pyrimidine (Compound VII)

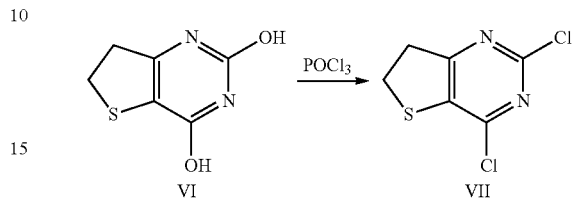

800 g of solid Compound VI (4.66 mol) was charged into to an inert and dry jacketed reactor (reactor 1) equipped with a temperature probe, mechanical stirrer and a dropping funnel. 1.5 liter (9.31 mol) Diethylaniline was charged over 30 min to 1 h keeping the temperature at or below 25° C. The internal temperature was brought up to 105-110° C. and 0.68 equiv. (868 ml, 34% of the total) of phosphorus oxychloride was added into the reactor (reactor 1) over 5-10 min. When the inside temperature began to decrease, the internal temperature was maintained at 110° C. and addition of the remaining $POCl_3$ (1.32 equiv. or 66% of the total) resumed over a period of 30-40 min. The internal temperature was adjusted to 105-110° C. and the mixture was stirred for 18-24 h or until complete (HPLC analysis). The mixture was cooled to 45° C. and THF (400 mL) was charged at 45° C. The above crude mixture was placed into a secondary dry vessel or reactor (vessel or reactor 2). 4.8 l of water was charged into the reactor 1 and cooled to 5° C. The crude reaction mixture (in reactor or vessel 2) is then slowly charged into reactor 1 containing water keeping the temperature at 5-10° C. The mixture was stirred at 5° C. for 30 min to 1 h and the resulting solid was collected by filtration. The cake was rinsed with water twice (1.6 l per rinse) and the cake was air dried in the funnel for 6-8 h to afford 964 g (92% w/w; 88% yield) of crude Compound VII. Dichloromethane (4.6 L) is charged into a 10 L reactor. Crude Compound VII and activated carbon (46.2 g) were charged into the reactor, the mixture is heated to 40° C. and stirred for 20 min. The resulting solution was collected by filtration through a filter media to remove charcoal. The cake was rinsed with dichloromethane twice (175 ml per rinse). The solution was concentrated under reduced pressure to a minimum stirrable volume and the remaining dichloromethane was chased away by distillation with a minimum amount of petroleum ether. Additional petroleum ether (1.3 l) was charged into the reactor, the mixture was cooled to 10° C. and stirred for 1 hr. The resulting solid was collected by filtration and the cake was rinsed with petroleum ether twice (150 ml per rinse). The cake was air dried in the funnel (suction) until it appeared dry. The resulting solid Compound VII was transferred to a suitable tared container and dried in an oven at 50° C. for 6 hr to get final product: $^1$H NMR (400 MHz, DMSO-d6) • 3.45-3.56 (m, 4H); $^{13}$C NMR (400 MHz, DMSO-d6) • 29.3, 36.5, 134.8, 151.0, 154.1, 175.9.

3.2 Generation of Example 1

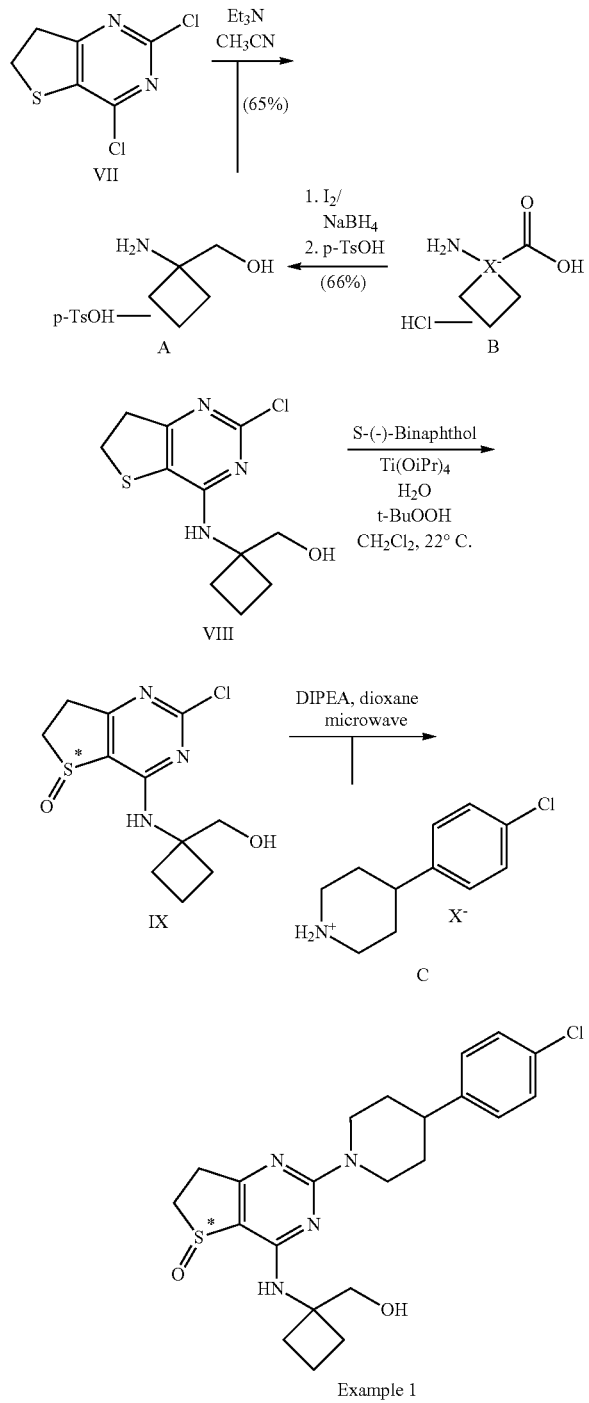

* chiral
X⁻ = Cl⁻ or Ts⁻ or HSO₄⁻

3.2.1 Synthesis of Compound A

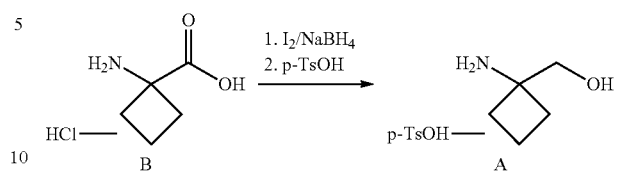

NaBH₄ (28.6 g, 757 mmol, 2.87 eq) and THF (500 ml) were charged to a 2 L reactor under nitrogen and the mixture was cooled to −5° C. A solution of I₂ (63.6 g, 251 mmol, 0.95 eq) in 125 mL THF was prepared and added to the reactor slowly over 45 min maintaining an internal temp of −5 to 5° C. The addition funnel was then rinsed with 42 mL THF. Compound B (50 g, 264 mmol, 1 eq) was then charged at −6° C., then the temperature rose to approx. 5° C. The reaction mixture was then heated to 65° C. for 23 h (Note: Reaction conversion was analyzed by GC/FID by quenching 0.1 mL reaction mixture with MeOH, then derivatizing with 0.5 mL of a 5/2/2 mixture of THF/acetic anhydride/TEA). 83 mL MeOH were then charged to the reaction mixture slowly over 20 min maintaining the temperature between 20-27° C. The reaction mixture was concentrated to a minimum stirrable volume and 500 mL 2-methyltetrahydrofurane (MeTHF) were added. 485 g of 25 wt % aq. NaOH (11.5 eq) were then added, solids were dissolved. The layers were separated and the aqueous phase was extracted twice with 500 ml 2-methyltetrahydrofurane (MeTHF). The organics were then filtered through a pad of celite and MgSO₄ and rinsed with 50 mL 2-methyltetrahydrofurane (MeTHF). A solution of p-toluenesulfonic acid monohydrate (51 g, 264 mmol, 1 eq) in MeTHF (100 ml) was prepared and added to the organics (alternatively HCl may be used to obtain the HCl-salt of compound A). A homogeneous light yellow solution resulted. The solution was concentrated to ~275-300 mL and the water content was checked. Additional MeTHF was added and concentrated to the original volume until the water content was <0.1%. The resulting solid was filtered and rinsed with 50 ml MeTHF, left to dry in the funnel overnight and then dried further in the vacuum oven at 50° C. 61.71 g of compound A were collected:

$^1$H NMR (DMSO-d6, 400 MHz) • 1.70-1.92 (m, 2H), 1.94-2.03 (m, 2H), 2.04-2.18 (m, 2H), 2.29 (s, 3H), 3.55 (s, 3H), 5.47 (br s, 1H), 7.13 (d, J=8.0 Hz, 2H), 7.49 (d, J=8.0 Hz, 2H), 7.95 (br s, 3H); $^{13}$C NMR (DMSO-d6, 100 MHz) • 13.3, 20.8, 56.4, 63.5, 125.5, 128.1, 137.8, 145.4

3.2.2 Synthesis of Compound VIII

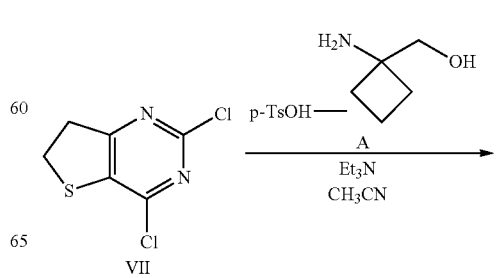

-continued

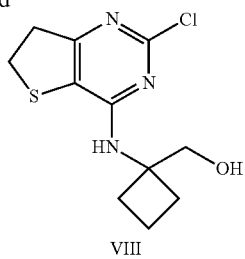

VIII

Intermediates VII (180 g, 852 mmol) and A (129 g, 937 mmol) were sequentially charged into a multi-neck vessel equipped with a condenser, thermocouple thermometer and nitrogen line. Acetonitrile (900 ml) and triethylamine (594 ml, 4.26 mol) were then added at 22° C. and the mixture was stirred at 75-77° C. for 12 h. Water (1.2 l) was charged slowly over 20 min, the mixture was seeded with Compound VIII crystals (0.3 g) at 40° C. and then cooled to 25° C. over 2 h. The mixture was stirred for an additional 12 h at normal room temperature and the resulting solid was collected by filtration. The filter cake was rinsed with 2:1 mixture of water/MeCN (400 mL) followed by water (200 ml). The resulting solid was dried under vacuum at 50° C. for 12 h to afford 132 g (57% yield) of compound VIII: $^1$H NMR (400 MHz, CDCl$_3$) • 1.85-2.05 (m, 2H), 2.10-2.21 (m, 2H), 2.32-2.41 (m, 2H), 3.27 (dd, J=8.0, 8.4 Hz, 2H), 3.43 (dd, J=8.0, 8.4 Hz, 2H), 3.91 (s, 2H), 4.67 (s, 1H); $^{13}$C NMR (CDCl$_3$, 100 MHz).14.8, 30.7, 31.2, 36.7, 59.7, 67.6, 114.7, 156.1, 156.2, 168.0.

3.2.3 Synthesis of Compound IX

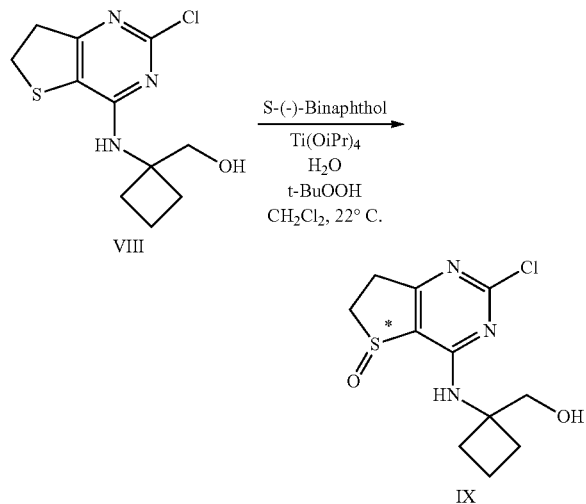

* chiral

Compound VIII (122 g, 429 mmol), S-(−)-1,1'-Bi-2-naphthol (S-(−)-BINOL) (12.4 g, 42.9 mmol), dichloromethane (608 mL), Ti(OiPr)$_4$ (6.54 mL, 21.4 mmol), and water (7.72 ml, 429 mmol) were charged to a 2 l multi-neck flask at 20° C. under nitrogen and stirred for 1 h. tert-Butyl hydroperoxide (70% in water, 62.3 ml, 472 mmol) was added at once at 21° C.; the mixture became completely homogeneous and the temperature rose to approx. 40° C. The mixture was allowed to reach normal room temperature, was stirred for 1.5 h and filtered. The cake was twice rinsed with isopropyl acetate (243 ml per rinse) and the cake was air-dried in the filter for >6 h to afford 114.4 g of compound IX.

$^1$H NMR (400 MHz, DMSO-d6) • 1.70-1.85 (m, 2H), 2.14-2.34 (m, 4H), 2.98-3.08 (m, 1H), 3.09-3.19 (m, 1H), 3.30-3.40 (obscured m, 1H), 3.50-3.62 (m, 1H), 3.65-3.77 (m, 2H), 4.91 (t, J=6 Hz, 1H), 8.63 (s, 1H); $^{13}$C NMR (100 MHz, DMSO-d6) • 14.5, 29.6, 29.8, 32.6, 48.6, 59.2, 62.8, 119.0, 157.8, 161.4, 175.3.

The other enantiomer of compound IX may be produced when S-(−)-1,1'-Bi-2-naphthol is replaced by R-(+)-1,1'-Bi-2-naphthol. A racemate of compound IX may be produced methods known by those skilled in the art that exclude chiral agents and conditions. An example for such a procedure to produce racemic sulfoxides is given in WO 06/111549.

3.2.4 Synthesis of Example 1

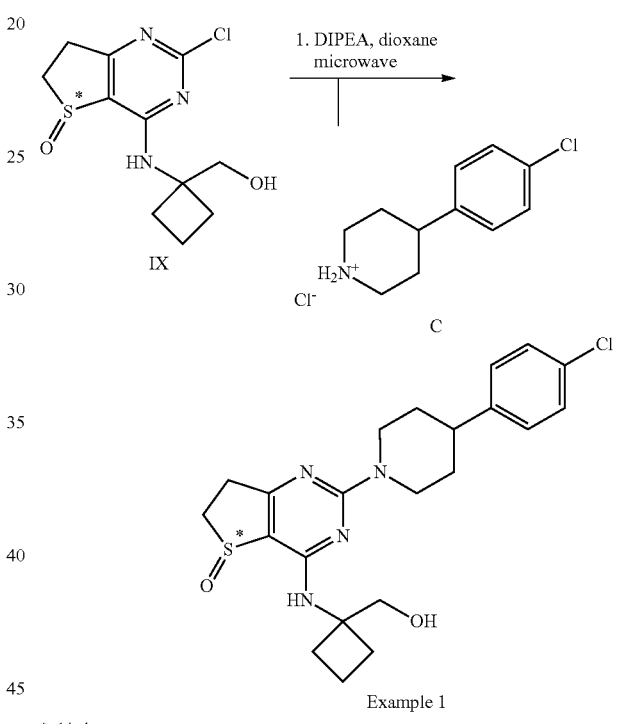

* chiral

Sulfoxide IX (6.48 g; 22.5 mmol), 4-(4-Chlorophenyl)-piperidine hydrochloride C (5.75 g; 24.8 mmol) (alternatively the p-TsOH-salt or the H$_2$SO$_4$-salt of compound C) and N,N-diisopropylethylamine (12.4 ml; 72.1 mmol) were mixed in 47 ml of dioxane. The resulting mixture was charged to three 20 ml vials which were heated to 120° C. for 25 min in a microwave oven. After cooling to room temperature, the reaction mixtures were poured on ice water. The resulting precipitate was filtered off, taken up in 500 ml ethyl acetate and heated to reflux. After refluxing, the mixture was cooled in an ice bath and the resulting precipitate was filtered off and dried in a dry box at 50° C. at reduced pressure yielding 7.57 g of Example 1.

$^1$H NMR (400 MHz, DMSO-d6) • 1.43-1.57 (m, 2H), 1.67-1.85 (m, 4H), 2.11-2.21 (m, 2H), 2.26-2.43 (m, 2H), 2.80-3.01 (m, 5H), 3.17-3.47 (m, integration compromised by water peak), 3.67-3.76 (m, 2H), 4.74-4.86 (m, 3H), 7.25-7.36 (m, 5H).

$^{13}$C NMR (100 MHz, DMSO-d6) • 14.3, 29.4, 29.6, 32.3, 32.5, 41.4, 44.2, 48.5, 58.4, 63.6, 109.2, 128.2, 128.6, 130.5, 144.7, 157.6, 161.5, 174.7

3.3 Generation of Example 2

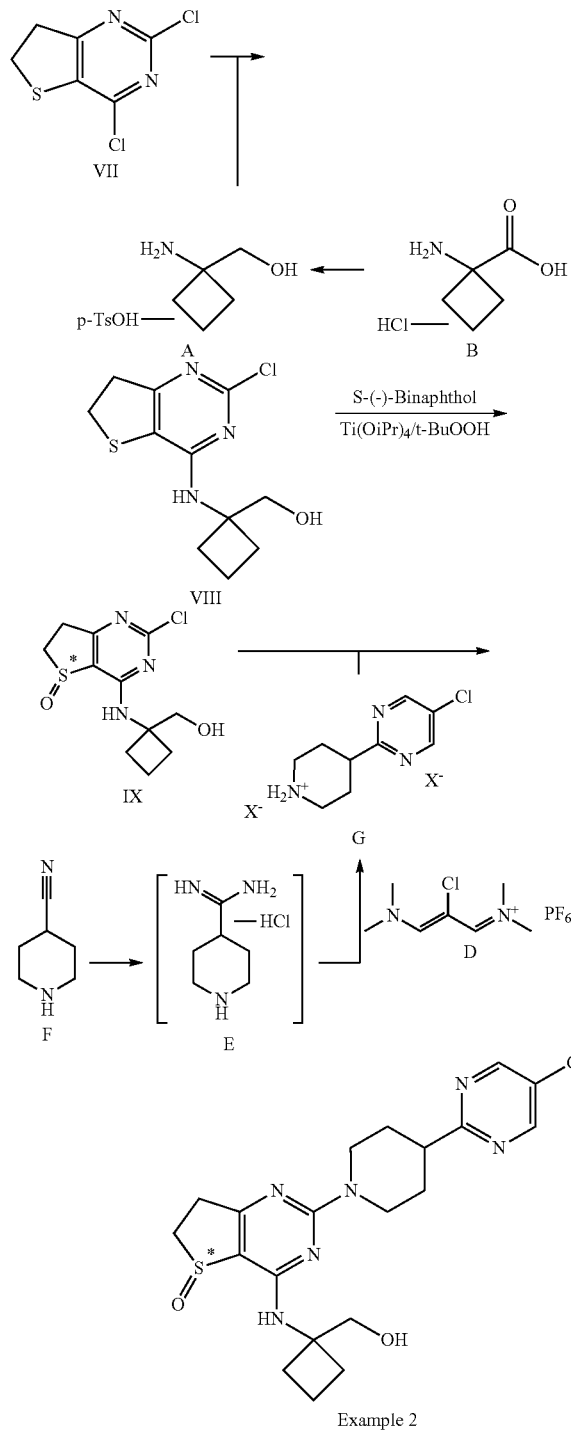

Example 2
* chiral
X⁻ = Cl⁻ or Ts⁻ or HSO₄⁻

3.3.1 Generation of Compound G

Scheme 5:

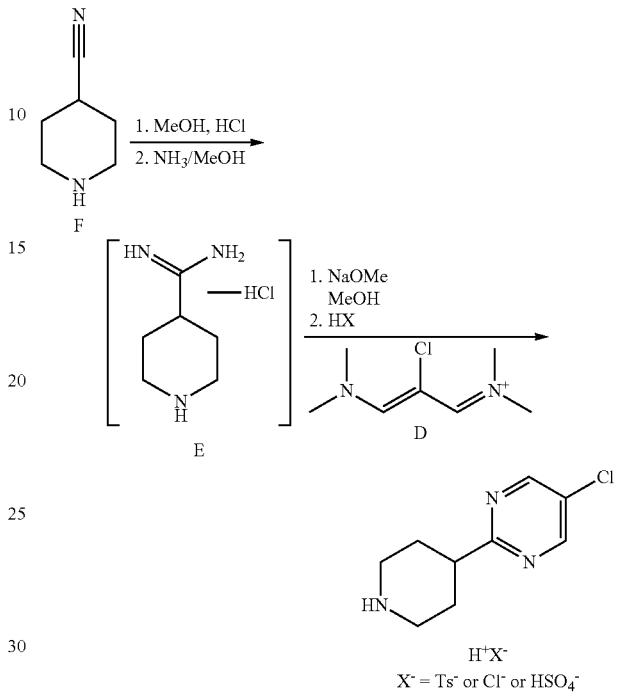

3.3.1.1 Synthesis of Compound E

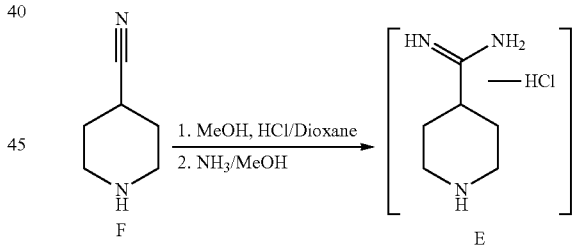

4M HCl in dioxane (225 ml, 3 eq, 900 mmol) was charged to a 500 ml 3-neck jacketed reactor equipped with a mechanical stirrer, temperature probe and argon line. The solution was cooled to 0° C. and 4-cyanopiperidine (33.04 g, 300 mmol) was charged followed by methanol (36.4 ml, 900 mmol, 3 equiv) over ~30 min while keeping the temperature below 10° C. (temperature rose). The above mixture was stirred for 6-8 h at normal room temperature until complete conversion was observed by $^1$H NMR analysis of an aliquot in D₂O (the clear solution turned into a white slurry after 30 min) The mixture was cooled to 5° C. and 25 wt % NaOMe in methanol (129.6 g, 600 mmol, 2 eq) was charged while maintaining the temperature below 15° C. The mixture was then stirred for 1 h. 7.0 N ammonia in methanol (64.2 ml, 1.5 eq, 450 mmol) was charged to the above mixture and stirred for 2 h at normal room temperature. The mixture was concentrated under reduced pressure at 60° C. to a volume of ~250 ml to afford a solution of crude compound E that was used without isolation:

$^1$H NMR (400 MHz, D$_2$O) • 1.80-1.95 (m, 2H), 2.15 (br d, J=4.4 Hz, 2H), 2.79-2.90 (m, 1H), 3.02 (ddd, J=13.2, 13.2, 3.0 Hz, 2H), 3.48 (m, 2H).

3.3.1.2 Synthesis of Compound G

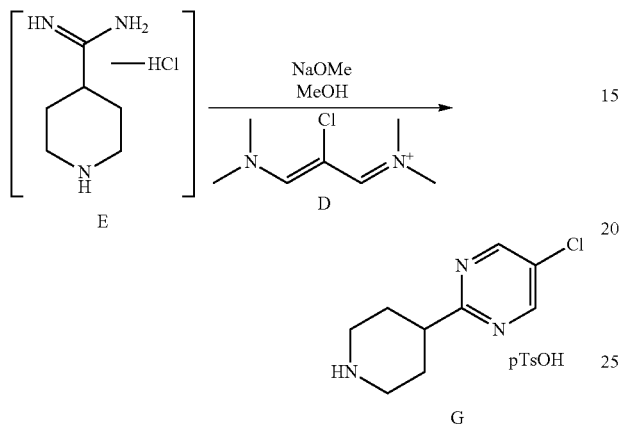

The above solution of intermediate compound E was cooled to ~20° C. and 25 wt % NaOMe in methanol (162 g, 2.5 eq, 750 mmol) was charged. The mixture was then stirred for 30 min Compound D (=(Z)—N-(2-chloro-3-(dimethylamino)allylidene)-N-methylmethan-aminium hexafluorophosphate (V)), (82.3 g of 95 wt % purity, 0.85 eq, 255 mmol) was charged to the above mixture in two portions at normal room temperature over ~30 min and stirred for 3 h at room temperature. The mixture was concentrated under reduced pressure at 60° C. to a volume of ~200 ml. 2-Methyltetrahydrofuran (400 ml) was charged and the mixture was concentrated further to a volume of ~150 ml under reduced pressure at 60° C. 2-methyltetrahydrofuran (250 ml) was charged, the mixture was cooled to ~20° C., water (150 ml) was added and the mixture was stirred for 5 min. The layers were separated and the organic layer was collected. The organic layer was washed with 30% aqueous NaOH (120 ml) and the layers were separated. The organics were concentrated to a minimum stirrable volume (~150 mL) and n-propanol (350 ml) was charged. A solution of p-toluenesulfonic acid monohydrate in n-propanol (0.85 equiv., 255 mmol, 48.4 g in 100 ml n-propanol) was charged to the above clear solution over 10 min at ~65° C. The above mixture was concentrated at ~65° C. under reduced pressure to maintain ~350 ml and <1.0% water (it is recommended to have a water content below 1.0% to avoid product losses to the mother liquor). The batch was cooled to 20° C. with stirring over 3 h. The solids were filtered, rinsed with the filtrate and then with n-propanol (120 mL) to afford 111 g (68% w/w by assay, 75.48 g) of compound G after vacuum drying at 65° C. in a vacuum oven for 12 h.

$^1$H NMR (DMSO-d6, 400 MHz) • 1.83-1.99 (m, 2H), 2.13 (d, J=12 Hz, 2H), 2.97 (s, 3H), 3.0-3.11 (m, 2H), 3.13-3.23 (m, 1H), 3.30-3.42 (m, 2H), 7.14 (d, J=8.0 Hz, 2H), 7.52 (d, J=8.0 Hz, 2H), 8.47 (br, 2H), 8.91 (s, 2H); $^{13}$C NMR (DMSO-d6, 100 MHz) • 20.7, 27.0, 40.8, 42.8, 125.5, 128.1, 128.8, 137.9, 145.2, 155.8, 169.0.

3.3.2 Synthesis of Example 2

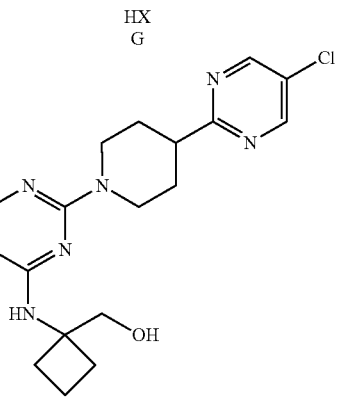

* chiral
with HX being HCl, TsOH or H$_2$SO$_4$

Compound IX (86.5 g, 291 mmol, 1 eq), compound G (160 g, 305 mmol, 1.05 eq), tetrahydrofuran (THF) (484 ml), water (121 ml) and DIPEA (N,N-diisopropylethylamine, 127 ml, 727 mmol, 2.5 eq) were all charged to a 3 l round bottom flask under nitrogen and heated to 65° C. for 3 h. Water (1125 ml, 13 ml/g compound IX) was then charged at the temperature 65° C. and stirred for 2 h while cooling to 20° C. The mixture was filtered and the cake was washed twice with 173 ml acetone. The cake was then left to dry on the funnel overnight to afford 116.7 g of Example 2:

$^1$H NMR (400 MHz, CDCl$_3$) • 1.75-1.95 (m, 4H), 2.02-2.11 (m, 2H), 2.12-2.26 (m, 2H), 2.38 (q, J=9.6 Hz, 2H), 2.93-3.12 (m, 4H), 3.12-3.22 (m, 1H), 3.28-3.39 (m, 1H), 3.53-3.65 (m, 1H), 3.80 (d, J=5.6 Hz, 2H), 4.42 (t, J=5.2 Hz, 1H), 4.82 (br d, J=11.2 Hz, 2H), 6.47 (s, 1H), 8.62 (s, 2H); $^{13}$C NMR (100 MHz, CDCl$_3$) • 14.8, 30.0, 30.1, 30.6, 32.7, 44.3, 49.4, 59.1, 68.2, 107.5, 129.1, 155.5, 159.0, 162.3, 170.5, 174.6.

3.3.2.1 Crystallization to Anhydrous Form A of Example 2

Preparation of Seed Crystals (Anhydrous Form A)

Small amounts of crude Example 2 (1-2 mg) were suspended in approximately 0.1 ml of the following solvents: ethanol, acetone, 2-butanone, ethyl acetate, isopropyl acetate, tetrahydrofuran, 1-propanol, 2-butanol, and acetonitrile.

After a heating/cooling cycle, the samples resulted in suspensions of crystalline anhydrous Form A as analysed by X-ray powder diffraction.

a. Crystallization from Acetic Acid, Dimethyl Sulfoxide, or N-Methyl-2-Pyrrolidone:

Approximately 1 g of crude Example 2 is dissolved in 10 ml of a polar organic solvent such as acetic acid, dimethyl sulfoxide, or N-methyl-2-pyrrolidone at a temperature of >60° C. The solution is cooled to 30-40° C. and an antisolvent (approximately 5-10 ml) such as isopropyl alcohol, ethyl alcohol, or acetone is added. The solution is seeded with anhydrous Form A crystals of Example 2 and cooled to 20° C. An additional amount of antisolvent (5-10 ml) is added to increase the yield. The resulting slurry is filtered within 1 hr of cooling and the wet cake is dried at 60° C. under vacuum. Anhydrous Form A is obtained as a white solid as confirmed by X-ray powder diffraction (XRPD) of the anhydrous Form A standard on file.

b. Crystallization from Tetrahydrofuran/Water:

Approximately 1 g of crude Example 2 is dissolved in 10 ml of tetrahydrofuran/water mixture (8:2, v/v) at a temperature of >60° C. The solution is cooled to 40-50° C., seeded with anhydrous Form A crystals of Example 2, and further cooled to 20° C. in less than 1 hr. Approximately 5-10 ml of antisolvent (an organic solvent such as isopropyl alcohol, ethyl alcohol, or acetone) is added to the slurry. The resulting slurry is filtered within 1 hr after the antisolvent addition and the wet cake is dried at 60° C. under vacuum. Anhydrous Form A is obtained as a white solid as confirmed by X-ray powder diffraction (XRPD) of the anhydrous Form A standard on file.

c. Drying from Dihydrate:

Approximately 1 g of the Dihydrate form of Example 2 is washed with approximately 5 ml of an anhydrous solvent such as ethanol, methanol, isopropanol, or acetone on a buchner funnel. The wet cake is then dried at 60° C. under vacuum. Anhydrous Form A is obtained as a white solid as confirmed by X-ray powder diffraction (XRPD) of the anhydrous Form A standard on file.

3.3.2.2 Crystallization to Anhydrous Form B of Example 2

Preparation of Seed Crystals of Anhydrous Form B

Small amounts of crude Example 2 (1-2 mg) were suspended in approximately 0.1 ml of 2-propanol and water mixtures (one with 3.3% of water and another with 6.6% water). After a heating/cooling cycle, the samples resulted in suspensions of crystalline anhydrous Form B by X-ray powder diffraction analysis. The samples in anhydrous 2-propanol subjected to the same conditions resulted in the mixture of Form A and Form B as analysed by X-ray powder diffraction. The mixture of Form A and Form B, slurried at 20° C. for 4 days in mixtures of water and the following solvents: methanol, ethanol, 2-propanol, 1-propanol, and acetone (all with approximately 9% water), resulted in Form B as analysed by X-ray powder diffraction.

a. Crystallization from n-Propanol/Water:

10 g of crude Example 2 is dissolved in 160 ml of n-propanol/water mixture (9:1, v/v) at a temperature of >65° C. The solution is cooled to 60° C., seeded with anhydrous Form B crystals of Example 2, and aged for 0.5 hr. The slurry is cooled to 30° C. over at least 5 hrs. Optionally the slurry is distilled at 30° C. under reduced pressure to reduce the volume to approximately 80-100 ml in order to maximize the yield. The slurry is further cooled to 0° C. and the slurry is aged for at least 8 hrs or until anhydrous Form A is no longer detected. The slurry is filtered and the wet cake is dried at 60° C. under vacuum. Anhydrous Form B of Example 2 is obtained as a white solid in a 90% yield. X-ray powder diffraction (XRPD) conforms to the anhydrous Form B standard on file.

b. Crystallization from Tetrahydrofuran/Water:

Approximately 1 g of crude Example 2 is dissolved in 10 ml of tetrahydrofuran/water mixture (8:2, v/v) at a temperature of >60° C. The solution is cooled to 40-50° C., seeded with anhydrous Form B crystals of Example 2, and is further cooled to 20° C. over 2 hrs. Approximately 10 ml of antisolvent (an organic solvent such as isopropyl alcohol, ethyl alcohol, or acetone) is added to the slurry. The resulting slurry is aged for at least 8 hrs or until anhydrous Form A is no longer detected. The slurry is then filtered and the wet cake is dried at 60° C. under vacuum. Anhydrous Form B of Example 2 is obtained as a white solid. X-ray powder diffraction (XRPD) conforms to the anhydrous Form B standard on file.

c. Conversion from Dihydrate:

Approximately 1 g of Dihydrate of Example 2 is suspended in 5-10 ml of an anhydrous solvent such as ethanol, methanol, isopropanol, acetone, ethyl acetate, isopropyl acetate, tetrahydrofuran, or acetonitrile. The suspension is seeded with anhydrous Form B crystals of Example 2 and stirred at 20-40° C. for at least 4 hrs or until the conversion to anhydrous Form B is complete as checked by X-ray powder diffraction (XRPD) analysis.

d. Conversion from Anhydrous Form A:

Approximately 1 g of anhydrous Form A of Example 2 is suspended in 5-10 ml of an anhydrous solvent such as ethanol, methanol, isopropanol, acetone, ethyl acetate, isopropyl acetate, tetrahydrofuran, or acetonitrile. The suspension is seeded with anhydrous Form B crystals of Example 2 and stirred at 20-40° C. for at least 4 hrs or until the conversion to anhydrous Form B is complete as checked by X-ray powder diffraction (XRPD) analysis.

3.3.2.3 Crystallization to Dihydrate Form of Example 2

Preparation of Seed Crystals of the Dihydrate Form

The mixture of anhydrous Form A and anhydrous Form B crystals of Example 2, slurried at 20° C. for 4 days in 2-butanone/water (with 9% water), resulted in the Dihydrate crystals as confirmed by X-ray powder diffraction analysis.

a. Crystallization from n-Propanol/Water:

10 g of crude Example 2 is dissolved in 120 ml of n-propanol/water mixture (8:2, v/v) at a temperature of >65° C. The solution is cooled to 50° C., seeded with Dihydrate crystals of Example 2, and aged for 0.5 hr. Water (approximately 60-100 ml) is added to the slurry. The slurry is cooled to 20° C. over at least 5 hrs and then aged for at least 8 hrs. The slurry is filtered, and the wet cake is washed with water and then air-dried.

b. Crystallization in THF/Water:

Approximately 1 g of crude Example 2 is dissolved in 10 ml of tetrahydrofuran/water mixture (8:2, v/v) at a temperature of >60° C. The solution is cooled to 30-50° C., seeded with Dihydrate crystals of Example 2, and further cooled to 20° C. over 2 hrs. Approximately 10 ml of water is added to the slurry. The resulting slurry is aged for at least 8 hrs. The slurry is filtered, and the wet cake is washed with water and then air-dried. X-ray powder diffraction (XRPD) of the product shows the Dihydrate pattern.

c. Conversion from Anhydrous Form A or from Anhydrous Form B:

Approximately 1 g of anhydrous Form A or of anhydrous Form B of Example 2 is suspended in approximately 5-10 ml of a mixture of at least 30% water and an organic solvent such as ethanol, methanol, isopropanol, acetone, or tetrahydrofuran. The suspension is seeded with Dihydrate crystals of Example 2 and stirred at 20° C. for at least 4 hrs or until the conversion to the Dihydrate Form is complete as checked by X-ray powder diffraction (XRPD) analysis. The slurry is filtered, and the wet cake is washed with water and then air-dried.

The polymorphs of Example 2 were characterized by X-ray powder diffraction (XRPD) as shown in FIGS. 3a, 3b and 3c showing the X-ray powder diffraction diagrams and the tables with all observable reflex peaks. For the performance of the X-ray powder diffraction analysis a Rigaku Miniflex II instrument was used with an X-ray generator of the type Power 450 W (30 kV-15 mA) (Optics: variable divergence slit). The Goniometer range was 3.0-35.0°2 • and the scan speed was 0.02° 2•/min with an accuracy of more than 0.01°. As a monochromator a foil filter/graphite was used and as a detector the scintillation counter NaI 23.0 mm diameter was used. The sample was analysed on a low background Si (510) sample holder.

The polymorphs of Example 2 were further characterized by differential scanning calorimetry (DSC) with a TA Instruments DSC Q1000 as shown in FIGS. 4a, 5a and 6a. The samples were analyzed in an unsealed Aluminium pan under an $N_2$ flow. The ramp that was used for the measurements was 10° C./min from 20° C. to 300° C.

The polymorphs of Example 2 were further characterized by thermogravimetric analysis (TGA) with a TA Instruments TGA Q500 as shown in FIGS. 4b, 5b and 6b. The samples were analyzed in an open platinum sample pan under $N_2$ flow. The ramp that was used for the measurements was 10° C./min from 20° C. to 300° C.

FIGURES

FIG. 1a: gastric emptying for rats that had received Example 1

Figure 1B:
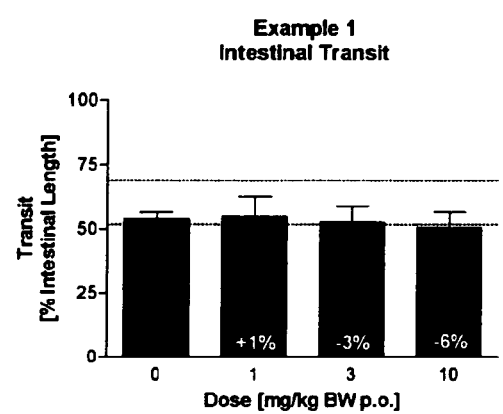

FIG. 1b: intestinal transit for rats that had received Example 1

Figure 2A:
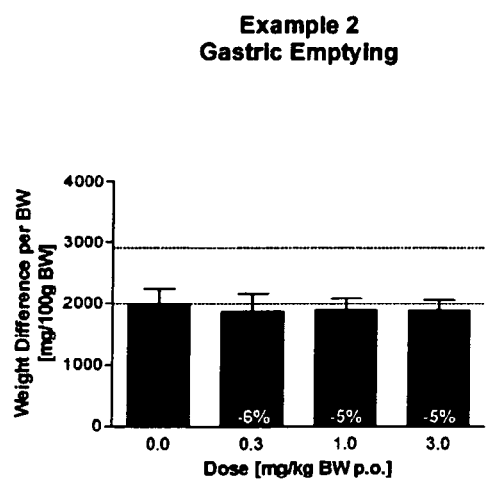

FIG. 2a: gastric emptying for rats that had received Example 2

Figure 2B:
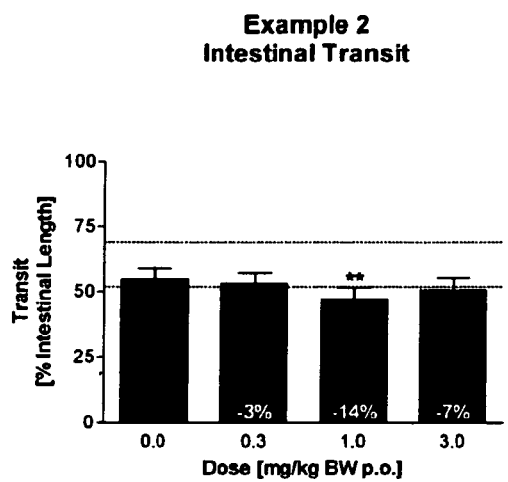

FIG. 2b: intestinal transit for rats that had received Example 2

FIG. 3a: X-ray powder diffraction diagram of anhydrous form A of Example 2

FIG. 3b: X-ray powder diffraction diagram of anhydrous form B of Example 2

FIG. 3c: X-ray powder diffraction diagram of dihydrate form C of Example 2

FIG. 4a: Differential Scanning calorimetrie (DSC) of the anhydrous Form A of Example 2 (DSC indicates a melt endotherm at about 235° C., followed by a decomposition when heating continued above melting)

FIG. 4b: Thermogravimetric Analysis (TGA) of the anhydrous Form A of Example 2 (TGA indicates non-solvated form as shown by negligible volatile content (minimal weight loss of (0.145%) up to the melting temperature)

FIG. 5a: Differential Scanning calorimetrie (DSC) of the anhydrous Form B of Example 2 (DSC indicates either a solid-solid transition or a simultaneous melt/recrystallization occurring at about 218° C. The resulting form is most likely anhydrous form A as indicated by the melt exotherm at 235° C., corresponding to the melting point of form A. After the melting of form A the compound is decomposed when heated above 240° C.)

FIG. 5b: Thermogravimetric Analysis (TGA) of the anhydrous form B of Example 2 (TGA shows negligible volatile content for form B (indicated non-solvated form) as shown by the minimal weight loss (0.057%) up to the melting temperature)

FIG. 6a: Differential Scanning calorimetrie (DSC) of the dihydrate Form C of Example 2 (DSC indicates low temperature dehydration as indicated by the broad endotherm at <100° C. The dehydrated solid is most likely form A as indicated by the melt endotherm occurring at about 236° C. characteristic of form A. Form A is then decomposed when heated above melting temperature), FIG. 6b: Thermogravimetric Analysis (TGA) of the dihydrate form C of Example 2 (TGA shows a large weight loss for form C indicating the dehydration by heating at <100° C. The dehydrated material (likely form A) shows almost no weight loss up to melting (from 100° C. to 236° C.) consistent with the previous observations for form A)

4 EXAMPLES

The following Examples were prepared analogously to the methods of synthesis described hereinbefore.

TABLE A

Chemical structures of the example compounds of the instant invention

| Example No. | Chemical Structure |
|---|---|
| 1 | 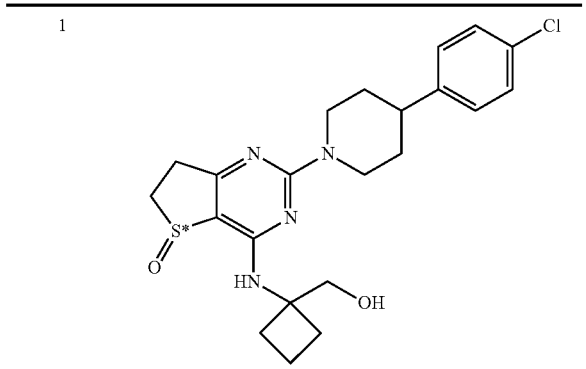<br>wherein S* stands for a sulphur atom which represents a chiral center |
| 2 | 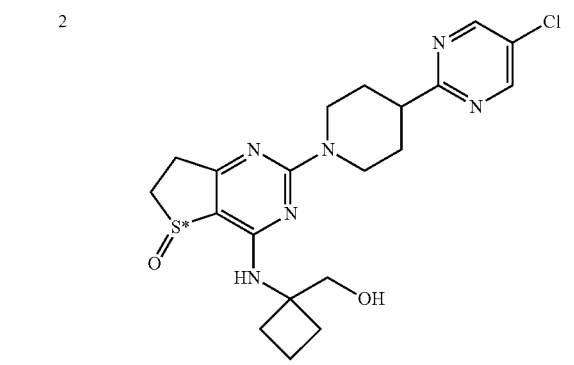<br>wherein S* stands for a sulphur atom which represents a chiral center |

The following Prior Art compounds A to D are the structurally closest compounds disclosed in WO 2009/050248 which is the closest piece of prior art.

TABLE B:

Chemical structures of the structurally closest compounds disclosed in WO 2009/050248.

| Prior art compound | Chemical Structure |
|---|---|
| Prior art compound A (= Example 2 of WO 2009/050248) | [Structure: thieno-pyrimidine with S*=O, HN-C(cyclopropyl)-CH2OH, and N-piperidinyl-4-chlorophenyl] wherein S* stands for a sulphur atom which represents a chiral center |
| Prior art compound B (= Example 27 of WO 2009/050248) | [Structure: thieno-pyrimidine with S*=O, HN-C(cyclopropyl)-CH2OH, and N-piperidinyl-imidazole] wherein S* stands for a sulphur atom which represents a chiral center |
| Prior art compound C (= Example 34 of WO 2009/050248) | [Structure: thieno-pyrimidine with S*=O, HN-C(cyclopropyl)-CH2OH, and N-piperidinyl-4-pyridyl] wherein S* stands for a sulphur atom which represents a chiral center |
| Prior art compound D (= Example 39 of WO 2009/050248) | [Structure: thieno-pyrimidine with S*=O, HN-C(cyclopropyl)-CH2OH, and N-piperidinyl-3-chlorophenyl] wherein S* stands for a sulphur atom which represents a chiral center |

5 BIOLOGICAL EXPERIMENTS

5.1 Determination of the PDE4B $IC_{50}$-Values (In Vitro)

The $IC_{50}$-values of the compounds of the invention (Example Compounds 1 and 2) and of the above-mentioned prior art compounds A to D with respect to their PDE4B-inhibiting ability have been determined with a Scintillation Proximity (SPA) Assay (GE Healthcare, No. TRKQ7090).

The Scintillation Proximity (SPA) Assay is based on the detection of the different affinities of the cyclic 3"-5"-adenosine monophosphate (cAMP, low affinity) and the linear 5'-adenosine monophosphate (AMP, high affinity) to yttrium-silicate-scintilator beads. The cAMP-specific phosphodiesterase (PDE) PDE4B cleaves the 3'-phosphodiester bond of the tritium-labelled-[$^3$H]cAMP to the [$^3$H]5'-AMP. This [$^3$H]5'-AMP associates with the scintillator beads because of their higher affinity and causes scintillations (light flashes) which can be measured in a Wallac Microbeta Scintillation Counter.

10 µl of a [$^3$H]cAMP-solution (0.05 µCi in $H_2O$, 10-30 Ci/mmol) are added to 89 µl of a PDE4B-enzyme-solution (active site fragment comprising the amino acids 152-484; 0.15-0.18 ng) in assay buffer (50 mM Tris HCl pH 7.5; 8.3 mM $MgCl_2$; 1.7 mM ethylene glycol tetraacetic acid (EGTA); 0.25 mg/ml bovine serum albumin (BSA)) and this mixture is incubated at 30° C. for one hour a) without the compound to be tested (in the presence of 1 µl dimethylsulfoxide (DMSO), corresponding to 1% DMSO) and b) in the presence of the compound to be tested in a concentration of 125 µM, 25 µM, 5 µM, 1 µM, 200 nM, 40 nM, 8 nM, 1.6 nM, 0.32 nM, 0.064 nM, 0.0128 nM (dilution series in 5er-steps beginning from 125 µM until 0.0128 nM, in the presence of 1% DMSO).

After this incubation the reaction is stopped by the addition of 50 µl of bead-solution (500 mg beads/35 ml $H_2O$, 18 mM zinc sulfate). In the following 45 minutes the beads have the opportunity to form a sediment. After that the scintillations are measured in the scintillation counter. If the tested compound is able to inhibit the enzymatic activity of the PDE4B- enzyme, less [$^3$H]AMP depending on the concentration of the tested compound is produced and less scintillations are measurable. These results are expressed as IC$_{50}$-values. The IC$_{50}$-value stands for the compound concentration at which the PDE4B enzyme activity is inhibited to a half maximal value. Therefore the lower the IC$_{50}$-value is the better is the PDE4B inhibition.

TABLE C

Experimentally determined IC$_{50}$-values with respect to PDE4B inhibition for the compounds of the invention and for the Prior art compounds as disclosed in WO 2009/050248

| Compound | Experimentally determined IC$_{50}$-value for PDE4B inhibition [nM] |
|---|---|
| Example 1 | 4.3 |
| Example 2 | 7.2 |
| Prior art compound A | 3.3 |
| Prior art compound B | 66 |
| Prior art compound C | 44 |
| Prior art compound D | 7.3 |

Only prior art compounds A and D have IC$_{50}$ values in the same potency range as Examples 1 and 2. Consequently all further experiments have been performed just with Examples 1 and 2 and with prior art compounds A and D.

5.2 Determination of the Dose Response Relationship and Calculation of the Half-Maximal Effective Dose in Regard to the Inhibition of LPS-Induced Neutrophil Influx into Bronchoalveolar Lavage Fluid of Male Wistar Rats The anti-inflammatory activity of Examples 1 and 2 and of Prior art compounds A and D was assessed in an in vivo LPS-induced lung inflammation model in rats.

As a measure of the pharmacological potency of the above mentioned compounds the half-maximal effective dose (ED$_{50}$) in regard to the inhibition of lipopolysaccharide-induced (LPS-induced) neutrophil influx into the bronchoalveolar lavage fluid (BALF) was determined by assessing the dose response relationship. Bacterial endotoxins (lipopolysaccharides [LPS]) are components of the outer bacterial cell membrane which play an important role in the pathogenesis of infections with gram-negative bacteria. It is known that inhalation of such aerosolized LPS induces a dose-dependent increase in neutrophils to lung tissues and airspaces in rats which may be detected by analyzing the amount of neutrophils in the bronchoalveolar lavage fluid (BALF). However, this dose-dependent increase of neutrophils in the BALF should be diminished in a dose-dependent way in the presence of an effective PDE4-inhibitor.

Male Wistar rats (HanWistar) from an approved local distributor were used for the experiments. The ordered weight of the animals was in the range of 200-250 g. Animals were fasted overnight before the experiment. A total number of 32 animals were used for each experiment. Eight animals (n=8) per dose were used for the treatment groups, two animals were used for the LPS-control (positive control) and two animals for the negative control.

The animals of the LPS-control and of the negative control groups received "vehicle only" ("vehicle only" corresponds to 10 ml/kg body weight 0.5% Natrosol solution). The other groups were treated with the different doses of either Example compound 1, Example compound 2, Prior art compound A or Prior art compound D respectively (see Table D).

The amount of compound for the highest concentration tested for each compound was suspended in 10 ml 0.5% Natrosol (Hydroxyethylcellulose) solution and then diluted to the respective concentrations as shown in Table D. The respective compound suspension or "vehicle only" (10 ml/kg body weight 0.5% Natrosol solution) was administered orally by gavage. The resulting doses of the individual compounds corresponded to Table D:

TABLE D

Tested compounds and their respective doses

| | | | | |
|---|---|---|---|---|
| Example 1 | 0.3 | 1.0 | 3.0 | 0.3 |
| Example 2 | 0.01 | 0.10 | 1.00 | 0.1 |
| Prior art compound A | 0.3 | 1.0 | 3.0 | 0.3 |
| Prior art compound D | 0.3 | 1.0 | 3.0 | 0.3 |

The above doses were determined due to previous tests in the LPS TNF Ex vivo mouse model.

One hour (0.5 hour for Prior art compound A and for Prior art compound D) after compound application (time set to allow for sufficient exposure as guided by prior pharmacokinetic experiments) the animals were exposed to nebulised/aerosolized LPS. The whole body exposure of 12 animals each was performed in a plexi glas chamber. Animals were separated/individualized with perforated metal plates. The aerosol was generated with a commercially available nebuliser (PARI Master+PARI LL nebuliser (Pari GmbH). The concentration of the nebulized LPS-solution was 1 mg/ml air. The duration of the LPS exposure was 30 minutes.

4 hours after the end of LPS exposure animals were anesthetised with Isoflorane and euthanised thereafter by cervical dislocation. The trachea was cannulated and BALF was performed using 2×5 mL lavage buffer (phosphate buffered saline (PBS)+2% BSA).

Determination of neutrophil content of the BALF was performed using an ADVIA 120 blood hemacytometer (Bayer Diagnostics). Neutrophil data were normalised (Positive Control (=LPS treatment alone)=100%, Negative Control (no LPS treatment, administration of "vehicle only")=0%) and expressed as percent of LPS control. The ED$_{50}$ was calculated using a nonlinear fit (with the Graph Pad Prism software and a sigmoidal dose response fit).

The ED$_{50}$-value is the half-maximal effective dosis of the compound in question with respect to its inhibition of an LPS-induced neutrophil influx into BALF. Consequently a very small ED$_{50}$-value stands for a good capability of the respective compound to prevent neutrophil influx into the lung tissue after LPS exposure and therefore for a good capacity of the respective compound to prevent inflammation of the lung tissue. Since the ED$_{50}$-value is unlike the IC$_{50}$ value not the result of an in vitro assay, but the result of an in vivo assay performed in rats and since here not only the direct inhibition of the PDE4B enzyme, but the neutrophil influx into the lung tissue after LPS-exposure is measured, the ED50 value is already a very sensitive parameter for a compound's suitability to serve as a therapeutic agent in inflammatory airway diseases like COPD and asthma (which are both inflammatory diseases).

Exposure of rats with LPS led to a distinct neutrophil influx into the BALF.

Pretreatment of rats with compounds Example 1, Example 2, Prior art compound A and Prior art compound D led to an inhibition of the LPS-induced neutrophil influx into the BALF. The calculated $ED_{50}$ values for the various compounds are given in Table E.

TABLE E $ED_{50}$ values of the tested compounds which were calculated from the experimental data:

| | |
|---|---|
| Example 1 | 0.31 |
| Example 2 | 0.1 |
| Prior art compound A | 1.13 |
| Prior art compound D | 6.66 |

The experimentally determined $ED_{50}$-values for the compounds of the invention—that means for Example 1 ($ED_{50}$=0.31 mg/kg body weight) and for Example 2 ($ED_{50}$=0.1 mg/kg body weight)—demonstrate that these compounds of the invention, Example 1 and Example 2, are between 3 to 66 times more potent in this assay than prior art compounds A and D.

Therefore the compounds of the invention show a better potency to prevent the influx of neutrophils into the lung tissue and are therefore a lot more suitable to be used as a therapeutic to treat inflammatory respiratory diseases such as asthma and COPD.

5.3 Gastric Emptying and Gastrointestinal Transit in Conscious Rats

In order to identify an active agent which is suitable to serve as a therapeutic PDE4 inhibitor it is necessary to determine whether the compound in question is effective at a dose that does not cause significant gastrointestinal side effects.

Gastrointestinal side effects are known to be prominent within the field of PDE4 inhibitors (see Diamant, Z., Spina, D.; "PDE4-inhibitors: a novel targeted therapy for obstructive airways disease", Pulm. Pharmacol. Ther. 2011, 24 (4), pp. 353-360 and Press, N.J.; Banner, K. H.; "PDE4 Inhibitors—A Review of the Current Field"; Progress in Medicinal Chemistry 2009, 47; pp. 37-74).

The experiments 1.1 and 1.2 above have shown that the compounds of the invention are clearly more potent with respect to PDE4B enzyme inhibition and/or more potent with respect to preventing neutrophil influx into the lung tissue and are therefore advantageous over the structurally related compounds disclosed in WO 2009/050248, in particular in comparison to Compounds A, B, C and D.

In order to evaluate whether the compounds of the present invention lead to gastrointestinal side effects the compounds of the invention have been administered to rats 30 minutes before the rats were fed with a test meal comprising barium sulfate. After that it was tested whether gastric emptying and/or gastrointestinal transit in these rats was affected by the presence of these compounds.

The effects of the compounds Example 1 and Example 2 on gastric emptying and gastrointestinal transit in conscious rats has been investigated as described below. Wistar rats of both sexes weighing 130-160 g (ages: male 7 wk, female 8 wk) were used. The animals are obtained from an approved local distributor, a minimum of four days quarantine is required before use, during which time the animals are maintained under routine animal care procedures. Groups of up to 5 animals are housed in cages in a room with controlled temperature and humidity and a light/dark cycle with the lights on from 6 a.m. to 6 p.m. The animals have access to normal rodent chow and water ad libitum. The animals are transported to the laboratory on the day of experimentation. Gastric emptying as well as small intestinal propulsion are determined using a barium sulfate test meal. Five rats Crl:WI(Han) of each sex (n=10) were used. The animals were deprived of food 17 h prior to the experiment but allowed free access to water.

The drug under investigation (drug was suspended to the concentration of 10 ml/kg body weight in 0.5% Natrosol solution) or the negative control (vehicle alone was given 10 ml/kg body weight) was administered 30 min. (p.o.) before the test meal at doses calculated to be 3-fold, 10-fold or 30-fold the $ED_{50}$ found in efficacy studies in the rat.

| Compound | Dose 3-fold $ED_{50}$ [mg/kg body weight p.o.] | Dose 10-fold $ED_{50}$ [mg/kg body weight p.o.] | Dose 30-fold $ED_{50}$ [mg/kg body weight p.o.] |
|---|---|---|---|
| Example 1 ($ED_{50}$ = 0.31 mg/kg BW) | 1.0 | 3.0 | 10.0 |
| Example 2 ($ED_{50}$ = 0.1 mg/kg BW) | 0.3 | 1.0 | 3.0 |

The test meal (suspension of 7.5 g barium sulfate in 10 ml salt-free water) is given orally by gavage at a dose of 2 ml/100 g body weight. Thirty minutes after the administration of the test meal the animals were killed in deep isoflurane anaesthesia by cervical dislocation. The stomach and the intestine were then exposed by laparatomy and removed.

The removed stomach was weighed, then incised, the contents removed and the empty stomach is weighed again.

The length of gut traversed with barium sulfate in relation to the whole length of the gut is determined by direct measurements using a ruler.

Evaluation of Gastric Emptying

The gastric content was calculated from the weight difference between the filled and empty stomach and normalized to 100 g body weight. Thus, an increase in weight difference indicated an impaired gastric emptying, whereas a decrease in weight difference indicated an enhanced gastric emptying.

Evaluation of Intestinal Transit

The length of gut traversed with barium sulphate (as judged by visual inspection) in relation to the whole length of the gut (from the pylorus to the rectum) is determined by direct measurements using a ruler.

Intestinal transit is calculated as the percentage movement of barium sulphate in the intestine in relation to the whole length of the gut. Consequently an increased intestinal transit length indicated an accelerated intestinal transit whereas a decreased intestinal transit length indicated decelerated intestinal transit.

Statistics

Data are expressed as mean±standard deviation (SD). For each dose, comparisons were performed using an analysis of variance (ANOVA) and a post hoc Dunnett test to compare the various groups to the controls when the ANOVA was significant. $p<0.05$ was considered significant.

Consequently the compounds of the invention show no statistically relevant gastrointestinal side effects, even at doses which are up to the 30-fold $ED_{50}$-dosis, because as shown in FIGS. 1a and b and 2a and b rats which had received either example 1 or 2 neither showed a substantially enhanced or impaired gastric emptying nor a substantially accelerated or decelerated intestinal transit even at doses up to 30-fold $ED_{50}$-dose.

For Example 1 the gastric emptying shows no relevant differences at a 3-fold $ED_{50}$ dose and at a 10-fold $ED_{50}$ dose, and only a very moderate enhancement of the weight difference per body weight at a 30-fold $ED_{50}$ dose. However, the intestinal transits for the corresponding animals which received Example compound 1 showed no significant differences compared to those intestinal transits of the negative controls even up to the 30-fold $ED_{50}$ dose.

For Example 2 both the gastric emptying and the intestinal transit showed no relevant differences compared to the negative control during all tested doses of Example compound 2, not even at the 30-fold $ED_{50}$ dose.

Consequently the compounds of the invention are not only more potent with respect to PDE4B inhibition than the compounds disclosed in WO 2009/050248 (as shown in Experiments 1.1 and 1.2), but also show no relevant gastrointestinal side effects.

6. INDICATIONS

The compounds of formula I have a broad potential in different therapeutic fields. Particular mention should be made of those applications for which the compounds according to the invention of formula I are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, inflammatory diseases of the joints such as rheumatoid arthritis or inflammatory diseases of the skin and eyes.

Preferential mention should also be made to the treatment of sarcoidosis.

Preferential mention should also be made of the treatment of cancers. Examples include all forms of acute and chronic leukaemias such as acute lymphatic and acute myeloid leukaemia, chronic lymphatic and chronic myeloid leukaemia as well as bone tumours such as e.g. osteosarcoma and all kinds of gliomas such as e.g. oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula I for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, alpha-1-antitrypsin deficiency, particularly COPD, chronic bronchitis and asthma.

It is most preferable to use the compounds of formula I for the treatment of inflammatory and obstructive diseases such as COPD, chronic bronchitis, chronic sinusitis, asthma, Crohn's disease, ulcerative colitis, rheumatoid arthritis, particularly COPD, chronic bronchitis and asthma.

It is also preferable to use the compounds of formula I for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

It is also preferable to use the compounds of formula I for the treatment of inflammatory diseases of the eyes, in particular for the treatment of the "dry eyes" syndrome and for the treatment of glaucoma. Individuals with the "dry eyes" syndrome suffer from ocular discomfort (dry, gritty feeling; itching; stinging/burning; pain/soreness) and blurred vision. The phosphodiesterase 4 (PDE4) enzymes regulate the biological processes of a host by degrading the second messenger cAMP. PDE4 inhibitors have been intensively investigated as antiinflammatory therapies because increases in cAMP levels are known to attenuate inflammatoy responses in multiple cell types (see Govek et al, Bioorganic & Med. Chem. Lett 20, (2010), pp. 2928-2932).

Furthermore it is also preferable to use the compounds of formula I for the treatment of diseases of the eyes, in particular for the treatment of glaucoma, since it has been shown that an increase in cAMP protects retinal ganglion cells from high intracellular pressure (IOP) induced cell death (see Seki T. et al, J Mol Neurosci. 2011 January; 43(1):30-4.), and an increase in cAMP is involved in the reduction of IOP (see Naveh N. et al., Br J Ophthalmol. 2000 December; 84(12): 1411-4), the main reason for the development of glaucoma.

7. COMBINATIONS

The compounds of formula I may be used on their own or in conjunction with other active substances of formula I according to the invention. If desired the compounds of formula I may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors, NSAIDS, COX 2 inhibitors, EP 4-receptor antagonists, DPP4-inhibitors or double or triple combinations thereof, such as for example combinations of compounds of formula I with one or two compounds selected from among EP 4-receptor antagonists, DPP4 inhibitors, NSAIDS, COX 2 inhibitors and corticosteroids, betamimetics, corticosteroids, PDE4-inhibitors, EGFR-inhibitors and LTD4-antagonists,
anticholinergics, betamimetics, corticosteroids, PDE4-inhibitors, EGFR-inhibitors and LTD4-antagonists,
PDE4-inhibitors, corticosteroids, EGFR-inhibitors and LTD4-antagonists
EGFR-inhibitors, PDE4-inhibitors and LTD4-antagonists
EGFR-inhibitors and LTD4-antagonists
CCR3-inhibitors, iNOS-inhibitors (inducible nitric oxide synthase-inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase inhibitors)
anticholinergics, betamimetics, corticosteroids, PDE4-inhibitors and MRP4-inhibitors. The invention also relates to combinations of three active substances, each chosen from one of the above-mentioned categories of compounds.

Suitable betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5.6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1.4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid, 8-{2-[2-(3.4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl-cyclopropyltropine 4,4'-difluorobenzilate methobromide, tropenol 9-hydroxy-xanthene-9-carboxylate-methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1, 4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370,N-(3,5-dichloro-1-oxo-pyridin-4-yl)-4-difluoromethoxy-3-cyclopropylmethoxybenzamide, (−)p-[(4aR*.10bS*)-9-ethoxy-1,2,3,4, 4a,10b-hexahydro-8-methoxy-2-methylbenzo[s][1.6] naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N—[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

EP 4 receptor antagonists which may be used are preferably compounds selected from among

[N-{[4-(5,9-diethoxy-6-oxo-6,8-dihydro-7H-pyrrolo[3,4-g] quinoline-7yl)-3-methylbenzyl]sulfonyl}-2-(2-methoxyphenyl)acetamide];

5-butyl-2,4-dihydro-4-[[2'-[N-(3-methyl-2-thiophene-carbonyl)sulfamoyl]biphenyl-4-yl]methyl]-2-[(2-trifluoromethyl)phenyl]-1,2,4-triazole-3-on;

(4-{(1S)-1-[({5-chloro-2-[(4-fluorophenyl)oxy] phenyl}carbonyl)amino]ethyl}benzoic acid;

N-[({2-[4-(2-ethyl-4,6-dimethyl-1H-imidazo[4,5-c]pyridin-1-yl)phenyl]ethyl}amino) carbonyl]-4-methylbenzol sulfonamide;

4-[[4-(5-methoxy-2-pyridinyl)phenoxy]methyl]-5-methyl-N-[(2-methylphenyl)sulfonyl]-2-furane carboxamide;

11alpha, 15alpha-dihydroxy-16-(3-methoxymethylphenyl)-9-oxo-17,18,19,20-tetranor-5-thia-13(E) prostanoic acid methyl ester;

4-cyano-2-[[2-(4-fluoro-1-naphthalenyl)-1-oxopropyl] amino]-benzene butyric acid and N-{2-[4-(4,9-diethoxy-1-oxo-1,3-dihydro-2H-benzo[f] isoindol-2-yl)phenyl]acetyl}benzene sulphonamide.

NSAIDS which may be used are preferably compounds selected from among Aceclofenac, Acemetacin, Acetylsalicylsaure, Alclofenac, Alminoprofen, Amfenac, Ampiroxicam, Antolmetinguacil, Anirolac, Antrafenin, Azapropazon, Benorilat, Bermoprofen, Bindarit, Bromfenac, Bucloxinsáure, Bucolom, Bufexamac, Bumadizon, Butibufen, Butixirat, Carbasalatcalcium, Carprofen, Cholin Magnesium Trisalicylat, Celecoxib, Cinmetacin, Cinnoxicam, Clidanac, Clobuzarit, Deboxamet, Dexibuprofen, Dexketoprofen, Diclofenac, Diflunisal, Droxicam, Eltenac, Enfenaminsáure, Etersalat, Etodolac, Etofenamat, Etoricoxib, Fecloxbuzon, Felbinac, Fenbufen, Fenclofenac, Fenoprofen, Fentiazac, Fepradinol, Feprazon, Flobufen, Floctafenin, Flufenaminsáure, Flufenisal, Flunoxaprofen, Flurbiprofen, Flurbiprofenaxetil, Furofenac, Furprofen, Glucametacin, Ibufenac, Ibuprofen, Indobufen, Indometacin, Indometacinfarnesil, Indoprofen, Isoxepac, Isoxicam, Ketoprofen, Ketorolac, Lobenzarit, Lonazolac, Lomoxicam, Loxoprofen, Lumiracoxib, Meclofenaminsáure, Meclofen, Mefenaminsáure, Meloxicam, Mesalazin, Miroprofen, Mofezolac, Nabumeton, Naproxen, Nifluminsáure, Olsalazin, Oxaprozin, Oxipinac, Oxyphenbutazon, Parecoxib, Phenylbutazon, Pelubiprofen, Pimeprofen, Pirazolac, Priroxicam, Pirprofen, Pranoprofen, Prifelon, Prinomod, Proglumetacin, Proquazon, Protizininsáure, Rofecoxib, Romazarit, Salicylamid, Salicylsaure, Salmistein, Salnacedin, Salsalat, Sulindac, Sudoxicam, Suprofen, Talniflumat, Tenidap, Tenosal, Tenoxicam, Tepoxalin, Tiaprofensaure, Taramid, Tilnoprofenarbamel, Timegadin, Tinoridin, Tiopinac, Tolfenaminsáure, Tolmetin, Ufenamat, Valdecoxib, Ximoprofen, Zaltoprofen and Zoliprofen.

COX2-inhibitors (Coxibe) which may be used are preferably compounds selected from among Celecoxib, Meloxicam, Etoricoxib, Lumiracoxib, Parecoxib, Rofecoxib and Valdecoxib.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichlorothieno[3,2-b]pyridin-5-yl-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}-amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}-amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}-amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)

carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl) amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl) carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl) amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl) amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl) methoxy]-quinazoline, 4-[(3-chloro-4-fluoro-phenyl) amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, cetuximab, trastuzumab, ABX-EGF and Mab ICR-62, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4] diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydrop-toluenesulphonates, preferably the hydrochlorides, hydrobromides, hydrosulphates, hydrophosphates, hydrofumarates and hydromethanesulphonates.

Compounds which may be used as iNOS inhibitors are compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrullin, S-ethylthiocitrulline, L-NA (N$^\omega$-nitro-L-arginine), L-NAME (N$^\omega$-nitro-L-argininemethylester), L-NMMA (N$^G$-monomethyl-L-arginine), L-NIO (N$^\omega$-iminoethyl-L-ornithine), L-NIL (N$^\omega$-iminoethyl-lysine), (S)-6-acetimidoylamino-2-amino-hexanoic acid (1H-tetrazol-5-yl)-amide (SC-51) (J. Med. Chem. 2002, 45, 1686-1689), 1400W, (S)-4-(2-acetimidoylamino-ethylsulphanyl)-2-amino-butyric acid (GW274150) (Bioorg. Med. Chem. Lett. 2000, 10, 597-600), 2-[2-(4-methoxy-pyridin-2-yl)-ethyl]-3H-imidazo[4,5-b]pyridine (BYK191023) (Mol. Pharmacol. 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-tifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. AR-C102222 (J. Med. Chem. 2003, 46, 913-916), (1S.5S.6R)-7-chloro-5-methyl-2-aza-bicyclo[4.1.0]hept-2-en-3-ylamine (ONO-1714) (Biochem. Biophys. Res. Commun. 2000, 270, 663-667), (4R, 5R)-5-ethyl-4-methyl-thiazolidin-2-ylideneamine (Bioorg. Med. Chem. 2004, 12, 4101), (4R,5R)-5-ethyl-4-methyl-selenazolidin-2-ylideneamine (Bioorg. Med. Chem. Lett. 2005, 15, 1361), 4-aminotetrahydrobiopterine (Curr. Drug Metabol. 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (Eur. J. Pharmacol. 2005, 509, 71-76), 3-(2,4-difluoro-phenyl)-6-[2-(4-imidazol-1-ylmethyl-phenoxy)-ethoxy]-2-phenyl-pyridine (PPA250) (J. Pharmacol. Exp. Ther. 2002, 303, 52-57), methyl 3-{[(benzo[1,3]dioxol-5-yl-methyl)-carbamoyl]-methyl}-4-(2-imidazol-1-yl-pyrimidin-4-yl)-piperazine-1-carboxylate (BBS-1) (Drugs Future 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (Drugs Future 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Compounds which may be used as SYK-inhibitors are preferably compounds selected from among:

2-[(2-aminoethyl)amino]-4-[(3-bromophenyl)amino]-5-pyrimidinecarboxamide;

2-[[7-(3,4-dimethoxyphenyl)imidazo[1,2-c]pyrimidin-5-yl]amino]-3-pyridinecarboxamide;

6-[[5-fluoro-2-[3,4,5-trimethoxyphenyl)amino]-4-pyrimidinyl]amino]-2,2-dimethyl-2H-pyrido[3,2-b]-1,4-oxazin-3 (4H)-one;

N-[3-bromo-7-(4-methoxyphenyl)-1,6-naphthyridin-5-yl]-1,3-propanediamine 7-(4-methoxyphenyl)-N-methyl-1,6-naphthyridin-5-amine;

N-[7-(4-methoxyphenyl)-1,6-naphthyridin-5-yl]-1,3-propanediamine;

N-[7-(2-thienyl)-1,6-naphthyridin-5-yl-1,3-propanediamine;

N-[7-[4-(dimethylamino)phenyl]-1,6-naphthyridin-5-yl]-1,2-ethanediamine;

N-[7-(4-methoxyphenyl)-2-(trifluoromethyl)-1,6-naphthyridin-5-yl]-1,3-propanediamine;

N-[7-(4-methoxyphenyl)-3-phenyl-1,6-naphthyridin-5-yl]-1,3-propanediamine;

N-(7-phenyl-1,6-naphthyridin-5-yl)-1,3-propanediamine;

N-[7-(3-fluorophenyl)-1,6-naphthyridin-5-yl]-1,3-propanediamine;

N-[7-(3-chlorophenyl)-1,6-naphthyridin-5-yl]-1,3-propanediamine;

N-[7-[3-(trifluoromethoxy)phenyl]-1,6-naphthyridin-5yl]-1,3-propanediamine;

N-[7-(4-fluorophenyl)-1,6-naphthyridin-5-yl]-1,3-propanediamine;

N-[7-(4-fluorophenyl)-1,6-naphthyridin-5-yl]-1,3-propanediamine;

N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-propanediamine;
N-[7-(T-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1, 1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]-N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;

3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
(1R.2S)—N-[7-[4-(dimethylamino)phenyl]-1,6-naphthyridin-5-yl]-1,2-cyclohexanediamine,
N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3'.5'-bis(trifluoromethyl) [1,1'-biphenyl]-4-yl]-1,6-naphthyridin-5-yl]0.3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylamino)phenyl]-1,6-naphthyridin-5-yl]-1,4-cyclohexanediamine;
7-[4-(dimethylamino)phenyl]-N-(2.2.6.6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1-methyl-1H-indol-5-yl)-1,6-naphthyridin-5-yl]-1,3-propanediamine;
N-[7-[3-(trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;
N-[7-[4-(4-morpholinyl)phenyl]-1,6-naphthyridin-5-yl]-1,4-cyclohexanediamine;
N-[7-[3-bromo-4-(4-morpholinyl)phenyl]-1,6-naphthyridin-5-yl]-1,4-cyclohexanediamine;
4-[[7-[4-[[2-(dimethylamino)ethyl]methylamino]phenyl]-1,6-naphthyridin-5-yl]oxy]-cyclohexanol;
N-[7-[3-bromo-4-(4-morpholinyl)phenyl]-1,6-naphthyridin-5-yl]-1,3-propanediamine;
N,N-dimethyl-4-[5-(4-methyl-1-piperazinyl)-1,6-naphthyridin-7-yl]-benzenamine;
4-[[7-[4-[[3-(dimethylamino)propyl]methylamino]phenyl]-1,6-naphthyridin-5-yl]oxy]-cyclohexanol;
N-[7-[4-[[2-(dimethylamino)ethyl]methylamino]phenyl]-1,6-naphthyridin-5-yl]-1,4-butanediamine;
1,1-dimethylethyl [3-[[5-[(3-aminopropyl)amino]-7-(4-methoxyphenyl)-1,6-naphthyridin-2-yl]amino]propyl]-carbamate.

The invention further relates to pharmaceutical preparations which contain a triple combination comprising a compound of formula I, II or III and two further active agents, both independently from one another selected from the above-mentioned groups of active agents such as another PDE4B-inhibitor, an anticholinergic, a betamimetic, a corticosteroid, an EGFR-inhibitor, a MRP4-inhibitor, an LTD4-antagonist, an iNOS-inhibitor, a PAF-antagonist, a H1-antihistamine, dopamin agonist, SYK inhibitor. The invention further refers to the preparation of such a double or triple combination and the use thereof for treating respiratory complaints.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e g lignin, spent sulphite liquors, methylcellulose, starch and polyvinylpyrrolidone) and lubricants (e.g. Magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula I dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof.

Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with dihydrothienopyrimidine and one or more combination partners selected from those described above.

The invention claimed is:

1. A method of making compound C

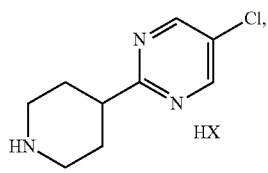

C wherein HX is tosylic acid, hydrochloric acid, or sulphuric acid, the method comprising:

A) first contacting 4-cyano-piperidine with an acid and then reacting with ammonia in order to obtain intermediate E

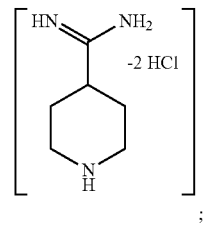

E

B) reacting intermediate E with compound D in the presence of a base

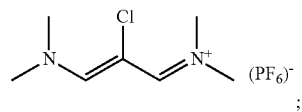

D and

C) adding the acid HX to obtain compound C.

2. The method of claim 1, wherein the acid in step A) is hydrochloric acid.

3. The method of claim 1, wherein the base in step B) is sodium methanolate.

* * * * *